United States Patent [19]
Zhou et al.

[11] Patent Number: 5,814,078
[45] Date of Patent: Sep. 29, 1998

[54] METHOD AND APPARATUS FOR REGULATING AND IMPROVING THE STATUS OF DEVELOPMENT AND SURVIVAL OF LIVING ORGANISMS

[76] Inventors: Lin Zhou; Xue-shan Zhang, both of 21 Carlos Dr., Fairfield, N.J. 07006

[21] Appl. No.: 395,042

[22] Filed: Feb. 28, 1995

Related U.S. Application Data

[60] Division of Ser. No. 827,636, Jan. 29, 1992, abandoned, which is a continuation-in-part of Ser. No. 508,302, Apr. 12, 1990, abandoned, which is a continuation-in-part of Ser. No. 103,808, Oct. 1, 1987, abandoned.

[30] Foreign Application Priority Data

| May 20, 1987 | [CN] | China | 87103603 |
| May 20, 1987 | [CN] | China | 87208158 |

[51] Int. Cl.⁶ ............................................. A61N 5/06
[52] U.S. Cl. ........................... 607/1; 607/88; 607/90; 607/96; 607/100
[58] Field of Search ................ 607/1–3, 88, 90, 607/96, 99, 100, 108, 113; 600/9, 26, 27, 28

[56] References Cited

U.S. PATENT DOCUMENTS

| 743,306 | 11/1903 | Merwin | 604/20 |
|---|---|---|---|
| 1,429,443 | 9/1922 | McFaddin | 128/395 |
| 3,658,068 | 4/1972 | McNall | 128/395 |
| 3,818,914 | 6/1974 | Bender | 128/396 |
| 3,821,576 | 6/1974 | Larson | 128/395 |
| 3,890,530 | 6/1975 | Hammer et al. | 313/489 |
| 3,967,153 | 6/1976 | Milke et al. | 313/492 |
| 3,995,191 | 11/1976 | Kaduk et al. | 313/489 |
| 4,287,554 | 9/1981 | Wolff | 362/218 |
| 4,420,709 | 12/1983 | Rattray | 313/487 |
| 4,505,545 | 3/1985 | Salia-Manoz | 350/321 |
| 4,540,915 | 9/1985 | Shinkai et al. | 313/486 |
| 4,588,700 | 5/1986 | Mutzhas | 28/395 |
| 4,601,917 | 7/1986 | Russo et al. | 106/287.19 |
| 4,607,191 | 8/1986 | Flaherty | 313/486 |
| 4,663,563 | 5/1987 | Taya et al. | 313/487 |
| 4,716,337 | 12/1987 | Huiskes et al. | 313/487 |
| 4,762,131 | 8/1988 | Okuda | 128/395 |

FOREIGN PATENT DOCUMENTS

| 85100593A | 6/1986 | China . |
| 05100538A | 8/1986 | China . |
| 1157584 | 5/1958 | France | 128/395 |
| 2846221A1 | 4/1980 | Germany . |
| 3027516 | 2/1982 | Germany | 128/395 |
| 3301802A1 | 1/1984 | Germany . |
| WO83/02233 | 7/1983 | WIPO . |

OTHER PUBLICATIONS

"Notices of Judgement under the FDA", Nov. 1951, p. 467.
"Luminescence of Alkaline—Earth Pyrophosphates, Activated with Divalent Europium," Aug. 1967, Wanmaker et al.
Health Dept. of Yunnan, China "Certificate of the clinical application and basic scientific research W5–Freq Spect. App.", Jun. 1983.

*Primary Examiner*—William E. Kamm
*Assistant Examiner*—Kennedy J. Schaetzle
*Attorney, Agent, or Firm*—Workman, Nydegger & Seeley

[57] ABSTRACT

A method and apparatus utilizing the action of simulated bio-frequency spectrum signals generated upon human beings, animals, plants, and micro-organisms to regulate and improve the status of growth and survival of said organisms. The simulated bio-frequency spectrum signals are generated through the excitation of one or a plurality of chemical elements and their compounds contained in the simulated bio-frequency spectrum signal generator by certain form of energy. Said simulated bio-frequency spectrum signals are broad band signals with wavelengths ranging from micrometers to centimeters. Said signals act upon certain sites of the organisms, elicit transition of the atoms, molecules, and electrons in the body of the organism, and cause resonances, thereby the aim of regulating and improving the status of growth of the organism is achieved.

1 Claim, 3 Drawing Sheets

1. ENERGY SOURCE
2. SIMULATED BIO-SPECTRUM GENERATOR
3. ENERGY TRANSDUCER
4. SIMULATED BIO-SPECTRUM GENERATING COMPONENT

METHOD AND APPARATUS FOR REGULATING AND IMPROVING THE STATUS OF DEVELOPMENT AND SURVIVAL OF LIVING ORGANISMS

RELATED APPLICATIONS

This is a divisional application of application No. 07/827,636, filed Jan. 29, 1992, now abandoned, which is a continuation-in-part application of application No. 508,302 filed Apr. 12, 1990, now abandoned, which in turn is a continuation-in-part of application No. 103,808 filed on Oct. 1, 1987, now abandoned.

THE FIELD OF THE INVENTION

The present invention relates to a method and apparatus for regulating and improving the status of development and survival of human beings, animals, plants, and microorganisms by means of a simulated or a partially simulated bio-frequency spectrum.

BACKGROUND OF THE INVENTION

Living organisms have unique physical and chemical properties. The elementary particles, such as molecules, atoms, and electrons are always vibrating and rotating. Living things are composed of molecules which rotate periodically, and electrons moving around the atoms, while the atoms or atom groups are vibrating. These activities form various energy levels and quantizations. The normal energy state of a molecule comprises the following energies:

$$E = E_o + E_n + E_r + E_v + E_e \quad (1\text{-}1)$$

wherein the energy changes related to the frequency spectrum of radiation of substances are: transitional energy of outer electrons of the nucleus, $E_e$; rotational energy of the molecule, $E_r$; energy of vibration of the atom, $E_v$. The corresponding ranges of these three kinds of energy levels are: 1–20 ev, 0.05–1 ev, and 0.0035–0.05 ev, respectively.

Molecules, atoms, and electrons constituting all substances radiate energies in the form of an electromagnetic frequency spectrum only during transitions of their energy levels. When the statuses of a living being change, the radiant energy and the frequency spectrum will change therewith, e.g. changes in cytomembrane potential, electrocardiograms, or electromyographs.

Molecules, atoms, or electrons have their own inherent frequencies. When they are subject to an electromagnetic radiation of a certain number of vibrations, $$V = N/C \quad (1\text{-}2)$$

where V is the number of vibrations, N is the frequency, and C is the velocity of light. If the applied electromagnetic frequency is equal to the inherent frequency of the molecules, atoms or electrons, a condition the same as that of the resonance in the case of vibration will occur; the molecules, atoms or electrons will absorb energy and transitions of energy levels can be elicited.

Bohr's quantum condition should be satisfied when molecules, atoms, or electrons transit from one energy level to another through the absorption of energy:

$$E_m - E_n = nV_{mn} \quad (1\text{-}3)$$

where $E_m$ and $E_n$ are high and low energy levels respectively. $V_{mn}$ is the number of electromagnetic vibrations.

Molecules, atoms, or electrons cannot absorb the electromagnetically radiated energy having the number of vibrations $V_{mn}$ if equation (1-3) is not satisfied. Since the energy levels of molecules, atoms and electrons are different and the number of vibrations are different too, the transitions of energy levels due to external electromagnetic radiation may be very complicated. The energy absorption will depend not only on the energy of the electromagnetic radiation but also on the wave number of the electromagnetic waves.

Living substances are also composed of molecules, but are more complicated in terms of energy status and structure. It has been found that a living organism is a good natural source of radiation. For example, 45% of the energy of a human body is dissipated in the form of radiant energy. When the temperature of the human body is 37° C., the maximum radiation is deduced from Wien's Displacement Law.

$$\max = \frac{2879}{310} = 9.35 \, \mu m$$

The inventor found through experiments that the band of human frequency spectrum is extremely broad; signals may appear in a band expanding from micrometers ($\mu$m) through millimeters (mm), and including near infrared, middle infrared, far infrared, and even millimeter waves. Experiments show that the human body is a comprehensive physical field, including a magnetic field, infrared radiations, and weak microwaves (mainly millimeter waves). The inventor holds that by using the "human spectrum" (FIG. 1, curve A) and according to Kirchoff's Law, it can be found that the absorption spectrum and radiation spectrum are essentially the same. That is to say that living organisms possess a physical field having certain frequencies and a spectrum which is called by the inventor "bio-frequency spectrum" or "bio-spectrum".

A part of the biofrequency is caused by light radiation by the living organism. This is the process by which chemical energy is effectively transformed into light energy by the organism. Light radiation by living organisms may also be called bioluminescence, which is a special case of chemical luminescence. The efficiency of bioluminescence is very high, i.e. the heat production is very low, so it is commonly called "cold light". A living organism has to acquire energy through the oxidation of certain easily oxidizable substances to maintain its life. Radicals containing oxygen, for example OH, may also be also be used to oxidize difficult to oxidize hydrocarbons, and biological chemical luminescence can be generated by certain reactions in that process. From microbes to humans, all living organisms luminesce at a low level. The spectrum is from 180 to 800 nm, the intensity falls into the range of $10$–$10^4$ nv/cm$^2$, and the quanta produced is only $10^{-14}$–$10^{-19}$. This kind of luminescence is linked with a number of biological processes such as oxidizing metabolism, detoxification, division and death of cells, photosynthesis, growth regulation, etc. Photographs of human luminescence can be taken. A normal human body luminesces mainly from the head; the color of the luminescence is orange-red tinted with a little bluish-green. Red light is emitted from all over the body of a man who is getting angry and forms a thick halo. The inventor suggests that this is due to leakage of the internal energy of the body. When the angry man is irradiated for 15 minutes with the apparatus of the present invention, he will feel relaxed and the anger is relieved. At this time, the red light around the body disappears from the photograph and the status of normal luminescence is resumed.

Cells of the organism can be affected by spectral radiation. Organic molecules generally absorb light with a wavelength longer than 200 nm, because the energy of the electrons of these molecules is no more than 140 Kcal/mol higher than that of the ground state electrons. Carotinoids absorb light with a 450 nm wavelength, while purine compounds absorb light with a 600 nm wavelength. Light with a 254 nm wavelength of a flux of $10^8$ photon/cm$^2$/s has been used to enhance glycolysis in yeast. Light with an 80 nm wavelength of a flux of $10^5$–$10^6$ photon/cm$^2$/s can accelerate the germination of synchronous yeast cultures.

It can be seen from the above that effects of bioluminescence, bio-spectrum, and light radiation of various wavelengths on living organisms are obvious. However conventional studies are still at a low level of understanding said effects and only touch on a very narrow spectral range or a single kind of radiation.

The present invention is capable of regulating and improving the growth of living organisms. As an example, when a human body is irradiated with the apparatus, the following regulative effects are produced:

1. An elongation of blood coagulation time and a decrease in blood viscosity at the same time can activate factor 10. An increase of prothrombin activity and activation of factor 8 at the same time can improve blood circulation, stop bleeding, relieve pain in wounds, and eliminate and cure inflammation.

2. Immunological reactions can be changed and phagocytic function enhanced. A marked increase in the total number of white cells and lymphocytes in peripheral circulation is achieved. Elimination of swelling is better than that in the control group ($P<0.01$).

3. Certain effects in stimulating the appetite, enhancing the development of the organism, decreasing the load on the heart, and the aggregation of blood platelets are achieved.

4. Local hypersensitivity and abnormal feeling caused by damage to the related peripheral nerves are eliminated. Conduction of the action potential of the nerves is partially recovered.

5. The apparatus has no direct germicidal effects on isolated bacteria, but effects on suppurative lesions and dermal ulcers caused by bacterial infection have been demonstrated in rabbits.

6. The present invention can cause a flowability increase of erythrocyte electrophoretic migration rate, morphotropism of red cell membranes, and a decrease in cell aggregation, which are advantageous to the improvement of the rheology of the blood and microcirculation.

7. In a diabetic rabbit model prepared with tetraoxy pyrimidine, after 1–2 courses of treatment (10 days/course) with the apparatus, the fasting blood-glucose concentration is decreased remarkably and the sugar tolerance curve shifts downwardly.

8. In experiments with a cerebral chemic mice model, the animals in a control group survived for 21.7 hours, while animals treated with the apparatus survived for 41 hours. Symptoms of cerebral ischemia were also milder in the treated group.

9. When patients with a disorder of the cervical vertebrae were irradiated with the apparatus, it was found through examination of nail fold microcirculation that the number of capillaries in the nail fold increased, the bore of the blood vessels was dilated, and blood flow was accelerated after 10 treatments. The improvement is significant ($P<0.001$) as compared with conditions before treatment.

10. The apparatus according to the invention is proven to have no deforming effects on mice chromosomes through examination of bone marrow smears.

11. The apparatus according to the invention can enhance the growth of microorganisms.

12. The apparatus according to the invention can protect living organisms from harmful irradiation.

13. The apparatus according to the invention can slow down the aging process.

Summarizing the above-mentioned experiments and research, the regulative and improving function of a simulated bio-spectrum on the status of growth of the human body can be briefly described as follows:

(1) It makes cells and tissues acquire energy and causes favorable changes in temperature, cell permeability, colloid status, flow rate of body fluids, acidity (pH value), enzyme system, and bio-electricity.

(2) It helps in improving and regulating the nervous system through excitation by simulated spectral energy. The sequence is: spectral energy→receptor→afferent nerve→nerve center→efferent nerve→effector. Regulative reflex arcs are thus formed to maintain biological balance of the human body, to eliminate diseases, and to enhance health. Because it functions through reflex of the nervous system, the apparatus can be placed at a distance from the site of a lesion and results in therapeutic effects on the whole body.

(3) An organism can produce certain metabolites and endocrine secretions by stimulation with simulated human spectral energy. These metabolites and endocrine secretions are conveyed by body fluids and act on various organs and systems to produce certain physiological regulative reactions and achieve therapeutic effects.

(4) After a nerve is stimulated by the physical field of the simulated bio-spectrum, blood and lymphatic circulations are accelerated, cell vitality and functions of organ systems are enhanced. Thus, the cell and humeral immunities are significantly enhanced.

(5) The signals of the physical field of the simulated bio-spectrum activate regulation of the nervous system, improve body fluid circulation, increase volume of the blood vessels, accelerate blood flow, improve blood supply to the heart, enhance peristalsis of the stomach, of the intestine, and of the body of gland, thus enhancing absorption by the digestive tract and maintaining optimal fraction thereof.

(6) The signals of the physical field of the simulated bio-spectrum stimulate nerves and body fluids to keep physiological balance through negative feedback and automatically perform a regulative function so that the important physiological indices of the human body (such as blood pressure, blood glucose, pH value, blood fat, membrane potentials of organs or cells) are controlled within normal range. Antagonistic symptoms like constipation and diarrhea, bleeding and hemostasis are also improved through the action of negative feedback.

In summary, the present invention can perform at least four distinct functions:

(1) Improving circulation of body fluids;
(2) Regulating the nervous system;
(3) Immunological function;
(4) Bio-negative feedback (bilateral regulation).

As human beings are concerned, the above four functions of the invention are sufficient to improve the status of growth, to treat many kinds of diseases, and to maintain good health to certain extents. The same functions can also be applied to other species of living beings.

In addition, it has been discovered that the method and apparatus using the simulated bio-spectrum can also be applied in biofeedback and in the field of oriental traditional medicine.

1. Application in the field of Chinese acupuncture and Jing-Luo (main collateral channels).

The method using the simulated bio-spectrum is capable of making "Qi" and "blood" flow freely, as well as making the main and collateral channels unblock (corresponding to improvements in the regulation of nerves and circulation in western medicine). To achieve the functions of regulation and treatment the apparatus of the present invention is used to directly irradiate the traditional acupoints, or a large area of the human body. The results are at least similar to those of other oriental traditional methods such as acupuncture and massage.

2. Application in "Qi-Gong" and "Yoga".

Because the function of the present invention is to cause resonating transition of the energy levels of the molecules, atoms, and electrons in the human body, the resonance excited through the acquisition of energy by the cell system reacts on tissues, organ systems, body fluids, and nerves, and forms a channel for information flow mainly in the form of sensory conduction. If trained with subconsciousness (practicing yoga or biofeedback), curious sensations of soreness, numbness, fullness, hotness or out crawling can appear at certain parts of the body. These changes can be detected with infrared spectrophotometry. The method of the present invention is applicable in the practice and research of "Qi-Gong" and "Yoga" for information therapy and health maintenance.

The present invention will help in making the exploration of oriental spirit, system, information, and "Qi-Gong" more scientific and standardized.

3. Application in the practice and training of biofeedback.

The principles of the invention can be used in biofeedback practice and training, which helps patients mobilize their intrinsic potentials, substantiate the content of psychotherapy, treat psychosomatic diseases, and train the handicapped extremities.

Up to the present, efforts have been made to control or affect the status of growth and to treat diseases of living beings by means of physical methods such as electrotherapy, ultrasound, infrared light, ultraviolet light, microwaves and lasers. These methods treat diseases with different physical factors, but all of these means are operating in a single or very narrow range of the spectrum and only result in the transition of energy levels in either molecules or atoms or electrons. Although these physical means may produce certain effects in living beings, the therapeutic effect is still at the lower level.

For example, an ultrasound therapeutic apparatus produces sound waves with frequencies over 20,000 Hz; an infrared therapeutic apparatus produces infrared light radiation with wavelengths of 0.72–25 $\mu$m; an ultraviolet apparatus produces ultraviolet rays with wavelengths of 189–380 nm; a microwave therapeutic apparatus produces ultra-high frequency electromagnetic waves with wavelengths of 1–100 mm, and laser treatments use monochromatic laser light to irradiate the human body. All of these methods have deficiencies in their therapeutic effects. The reason is that various physical factors do not match with the spectrum of the human body. The natural frequencies of the molecules, atoms and electrons in the human body are different from those produced by the various methods, thus cells in the human body are not able to acquire energy or to improve metabolic functions more effectively. Thus, the health of the human body is not effectively controlled.

SUMMARY OF THE INVENTION

The inventor found through experiments that the status of growth and energy of living beings can be regulated and controlled better only when the energies of the molecules, atoms, and electrons in such living beings are all changed and turned into resonance.

Therefore, the object of the present invention is to provide a method for regulating and improving the status of growth of living organisms which affects the growth and survival of living organisms. This is accomplished by introducing signals containing simulated bio-frequency spectrum in the living organisms, including human beings, animals, plants, and microbes, to make them match with the inherent spectrum of the organisms.

Another object of a invention is to provide an apparatus for regulating and improving the status of growth of the living organisms which can radiate a simulated bio-frequency spectrum similar to the inherent spectrum of the living organisms. Applying such a spectrum to certain portions of a living organism and having it matched with the inherent frequencies of and absorbed by the organism will result in producing high level regulative reactions and in achieving regulation and improvement of the status of growth and survival of the living organism.

The method for regulating and improving the status of growth of the organisms according to the present invention comprises the steps of:

a) Detecting and measuring the signals containing the inherent spectrum of the organism;

b) Simulating the signals containing the inherent spectrum of the organism and producing simulated signals identical with, similar to, or partially similar to the signals containing the inherent spectrum of the organism;

c) Applying said simulated bio-spectrum signals to the organism to cause transitions of energy levels of the elementary particles of the organism and to elicit resonance of the elementary particles, and hence to achieve a biological effect in favor of the regulative function within the organism.

The apparatus for regulating and improving the status of growth of organisms according to the present invention comprises:

Energy generating means; means for receiving the energy generated by said energy generating means and generating simulated bio-spectral signals identical, similar, or partially similar to signals containing the inherent spectrum of the organism; said simulated biospectrum signal generating means comprising one or a plurality of chemical elements and their compounds which are capable of generating said simulated bio-spectral signals.

The method and apparatus according to the present invention have two features:

1. The apparatus can produce electromagnetic radiation having a very broad spectrum, which covers the visible light band, the near and far infrared bands, the ultrafar infrared band, the submillimeter wave band, and possibly the centimeter wave band, i.e. completely covers the frequency wave band of the inherent natural oscillations of the organisms.

2. The intensities of the electromagnetic radiations are different at different bands of the spectrum, thus the biological effects they elicit are also different. Those eliciting thermal biological effects are in the range of visible light, near, middle and far infrared. They account for more than 90% of the radiated energy. Those eliciting nonthermal biological effects are ultrafar infrared, submillimeter waves and millimeter waves which occupy a broad frequency range but a low amount of radiant energy. Measurement with a millimeter wave detector shows that the radiant energy in the range of millimeter waves can be added directly to the weak radiant energy in the millimeter wave band of the organism for they belong to the same order of magnitude. Non-thermal biological effects are produced by the excitation of the resonance of the external electromagnetic radiation with the elementary particles in the living substances.

The above two features of the method and apparatus of the present invention make it possible to solve the following problems:

1. Combining the easily acquirable thermal effect with the non-easily acquirable non-thermal effect brings about good results in the regulation and improvement of growth of the living organisms.

2. The non-thermal biological effect is significant, but difficult to acquire under the low field intensity and low energy conditions of normal temperature and normal pressure. However, the present invention achieves non-thermal biological effects in the submillimeter, the millimeter, and possibly in the centimeter wave bands with extremely weak radiant energy which is far below the safety standards for electromagnetic waves in many countries and, therefore, will not cause damage to the living organisms.

These two features are significant to produce meaningful, complicated biological and physiological processes including neuro-humeral regulation and comprehensive regulative reactions of individual cells and tissue systems, which bring the functions of the organism into full play and cure diseases.

BRIEF DESCRIPTION OF THE DRAWINGS

FIGS. 4A-1, 4A-2, 4B-1, 4B-2, 4C-1, 4C-2 and 4D diagrammatically illustrate embodiments of the simulated bio-frequency spectrum generator according to the present invention;

DETAILED DESCRIPTION OF THE PREFERRED EMBODIMENTS

Figure 1:
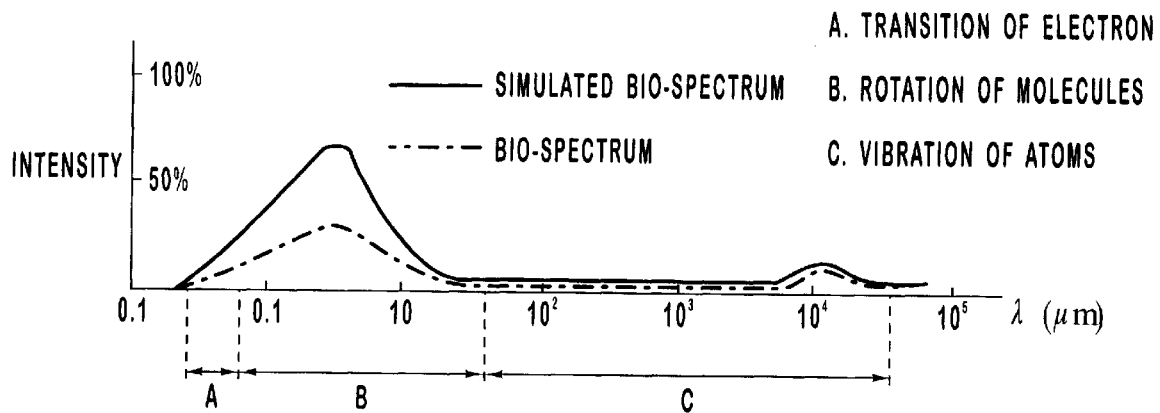
FIG. 1 schematically shows the inherent bio-frequency spectrum of the living organism and the simulated bio-frequency spectrum produced in accordance with the present invention.

In FIG. 1, the broken line denotes the range of distribution of the inherent bio-spectrum, with wavelengths ranging form 0.2 $\mu$m to 100,000 $\mu$m. The solid line denotes the simulated bio-spectrum generated according to the present invention, wherein 0.45–0.72 $\mu$m is the spectral range for eliciting transition of the electrons; 0.72–50 $\mu$m is the spectral range for eliciting rotation of molecules; 50 $\mu$m—several cm is the spectral range for eliciting transition of atoms.

Figure 2:
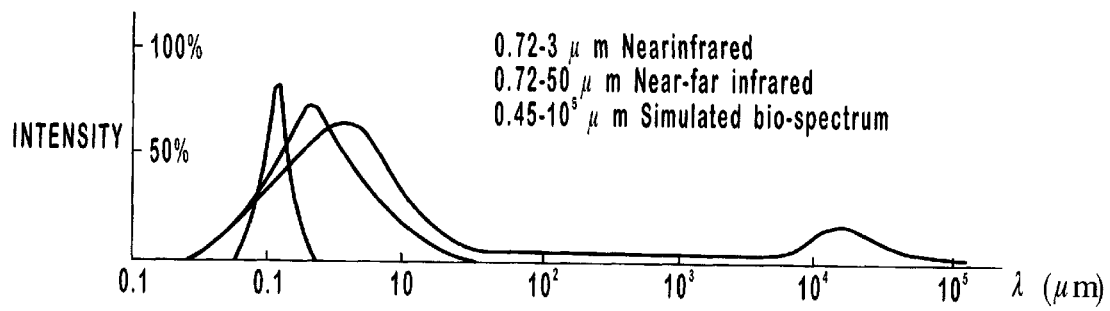
FIG. 2 schematically shows the simulated bio-frequency spectrum produced in accordance with the present invention and the spectrum produced with the conventional physical means.

FIG. 2 shows one of the current infrared devices (0.72–3 $\mu$m) which covers a very short band of the inherent bio-spectrum. The biological effect is mainly thermal. Another one of the current far infrared devices (0.72–50 $\mu$m) radiates a wider range of infrared spectra but still a short range in the inherent bio-spectrum. Its main biological effect remains in the thermal effect. The method and apparatus of this invention which matches the inherent bio-spectrum can generate a very broad range of frequency spectra (0.45–$10^5$ $\mu$m) The method and the apparatus of this invention can induce more profound biological effects which include thermal and non-thermal effects.

Figure 3:
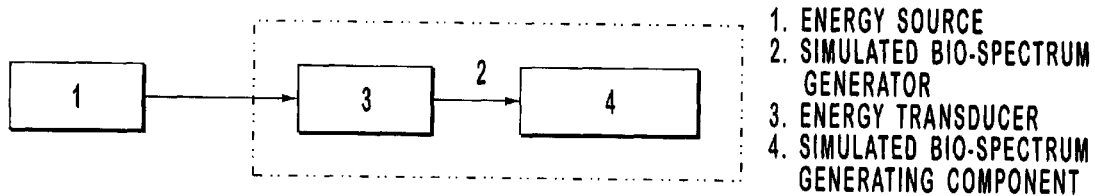
FIG. 3 is the schematic diagram showing the apparatus for regulating and improving status of growth of the organism according to the present invention.

FIG. 3 is the apparatus for regulating and improving the status of the living organism according to the present invention. In FIG. 3, 1 represents the energy source; 3 represents the energy transducer; 4 represents the simulated bio-spectrum generating component; energy transducer 3 and generating component 4 constitute the simulated bio-spectrum generator 2. The energy source can be of many forms, such as electrical energy, thermal energy, magnetic energy, solar energy, chemical energy, or biological energy, etc. Electrical energy is preferable because it is easy to acquire. The energy generated by the energy source is transduced into thermal or magnetic energy by the energy transducer to provide energy to the simulated bio-spectrum generating component. The simulated bio-spectrum generating component is composed of monomers or compounds of one or more chemical elements in the periodic table. Upon excitation by the energy, the transitions of energy levels of the elements or their compounds are emitted in the form of electromagnetic radiation to form a physical field of simulated bio-spectrum that acts on the organism through radiation. When it matches with the strong absorption band of the organism, a large portion of the radiant energy carried by the electromagnetic wave is absorbed, causing changes of the energies of molecules, atoms or electrons in the living organism, which then elicits oscillation, enhances bio-oxidation and improves energy of the cells to increase the permeability of cell membranes. With millions and millions of cells reacting in this manner, an integrated biological effect is formed which increases the circulation of body fluids, improves the regulative function of the nervous system, enhances photosynthesis, and finally, engenders effects in favor of the regulation of growth of the organism. As for the human body, the above four kinds of functions are provided at the same time.

Figures 1, 4A:
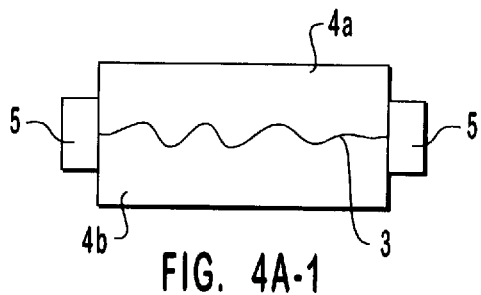
Figures 2, 4A:
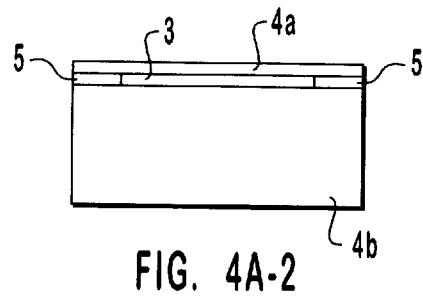
Figures 1, 4B:
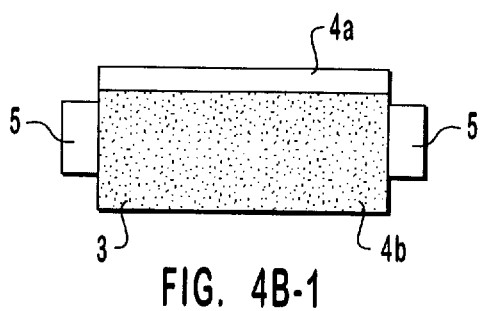
Figures 2, 4B:
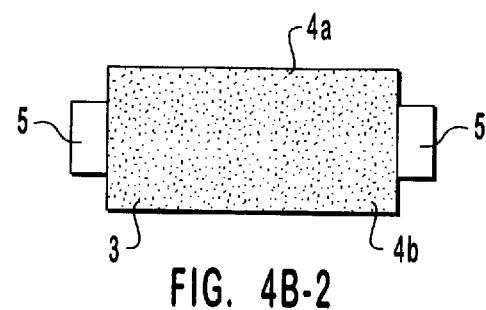
Figures 1, 4C:
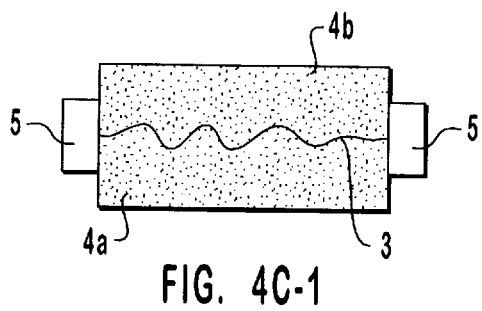
Figures 2, 4C:
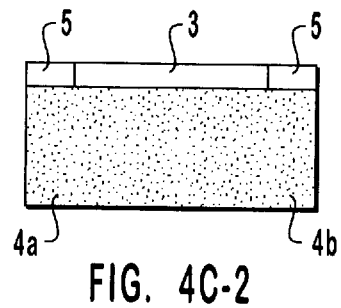
Figure 4D:
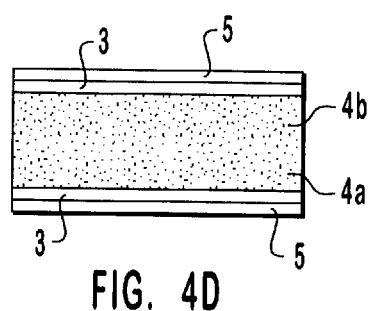

FIGS. 4A-1–4D show the embodiments of the simulated bio-spectrum generator according to the present invention. In FIG. 4A-1, the simulated bio-spectrum generating component comprises a substrate 4b and an emitting layer 4a disposed on the substrate and composed of borides, nitrides, carbides, sulfides, or fluoride. 5 is the electrode. The proportions of these elements and their compounds are determined depending upon the kind of organism to be regulated and its status of growth. This will be described in detail later. Substrate material is selected according to the type of energy source, which is an electrical power source in this embodiment. The substrate can be made from non-metal materials, such as ceramics with low hygroscopic properties, high heat resistance, high mechanical strength, high radiance; or from heat resistant (<150° C.) plastics with high radiance; or quartz glass, micro crystal glass, or other kinds of glass with high heat resistance and high strength. It can also be made from electric materials such as carbon rods or resistors which have high electric conductivity and are capable of reaching heat producing temperatures. Various kinds of chemical elements and their compounds are mixed in the right proportion, and then diluted into liquid adhesive, or they may be made into a coating material or enamel pulp and coated onto the surface of the substrate to form the emitting layer. Energy transducer 3 can be an electric heating wire or the like which is embedded into the substrate (as shown) or disposed on the ends of the substrate to convert electric energy into thermal energy. The heat generated by the heating wire is used to excite the chemical elements in the emitting layer. The temperature should not be lower than the body temperature of the living organisms.

The heating wire 3 in FIG. 4A-1 an be replaced by a layer of conducting membrane 3 (FIG. 4A-2) formed on the surface of the substrate by means of a metal oxidation technique (high temperature hydrolysis of chlorides to form a conducting membrane of metal oxides) to make the simulated bio-spectrum generator more solidified, thus increasing the speed and efficiency with which the electric energy is converted into thermal energy (FIG. 4A-1). In FIG. 4A-2, the emitting layer 4a is coated on the surface of the conducting membrane.

FIG. 4B-1 is another embodiment of the simulated bio-spectrum generator according to the present invention. In this embodiment, substrate 4b is integrated with the energy transducer 3 in a manner that the conducting substrate is infiltrated into non-metal material to make it electrically conductive and have satisfactory resistance. The emitting layer 4a is then coated onto the substrate to form a simulated bio-spectrum generator. The substrate can also be made from metals. In this case, electric current introduced into the substrate is converted into thermal energy and the substrate acts as the energy transducer at the same time. Then a layer of enamel pulp mingled with one or more chemical elements and their compounds in the right proportion is coated onto the metal substrate and sintered under high temperature to form a simulated bio-spectrum generator of metal substrate.

In FIG. 4B-2, the chemical elements and their compounds constituting emitting layer 4a can also be doped into substrate 4b and then sintered under high temperature to form a simulated bio-spectrum generator (FIG. 4B-2) which is even more integral than that of FIG. 4B-1, and shown in FIG. 4B-2.

FIG. 4C-1 is still another embodiment of the simulated bio-spectrum generator according to the present invention. In this embodiment, one or more chemical elements and their compounds are mixed in the right proportions with pot clay and sintered into an integral body so that the substrate per se contains the constituents that generate the simulated bio-spectrum. When an energy transducer such as an electric heating wire is embedded into the substrate, an integrated simulated bio-spectrum generator is formed.

In FIG. 4C-2, a conducting membrane 3 can be plated onto the surface of substrate 4b containing the chemical elements of emitting layer 4a. Conducting membrane 3 replaces the heating wire 3, and makes the simulated bio-spectrum generator a more integral body as show in FIG. 4C-2.

FIG. 4D is still another embodiment of the simulated bio-spectrum generator according to the present invention. In this embodiment, temperature resisting glass is used as the material of the substrate and one or more chemical elements and their compounds are mixed in the right proportions into the raw glass during sintering. A special glass body containing the constituents that generate the simulated bio-spectrum is formed by sintering. Then a layer of semiconductor membrane is formed on the surface of the glass as the energy transducer by means of metal oxidation, thus forming a colorless and transparent simulated bio-spectrum generator. In this embodiment, the material of the substrate can also be pot clay containing one or more chemical elements and their compounds so that the substrate per se contains constituents that generate the simulated bio-spectrum. An integrated solid ceramic simulated bio-spectrum generator is formed by disposing a layer of conducting membrane of metal oxides on the surface of such a substrate as an electrically conducting energy transducer.

The substrate can be made from either permanent or electric magnetic materials. In this case, the emitting layer is plated onto the magnetic substrate and a non-thermal simulated bio-spectrum generator made from magnetic material is formed.

The chemical elements to be used in the simulated bio-spectrum generator are selected in accordance with the following principles:

a. The spectrum of radiation of the chemical elements after acquiring energy should be distributed as widely as possible between the micrometer band and the millimeter band. If the radiation is only in the micrometer (infrared) band or only in the millimeter band, the biological effects produced are not good enough. In order to make the produced biological effects favorable to the growth and development of the living organisms, radiant signals should be present all over the range from micrometers to millimeters. Therefore, a broad spectrum of $\mu$m–mm is a distinct feature of the apparatus of the present invention. Selection and proportion of the chemical elements are indispensable to the realization of the broad frequency spectrum and are based on the fact that the elements must be able to generate a spectrum approximating the bio-spectrum when excited by energy.

b. The elements should be technically as similar to the chemical constituents of the bio-substances in the living organism as possible. The frequency distribution of the inherent bio-spectrum of the organism is then considered.

The chemical elements the present invention concerns include most of the elements of the 2nd, 3rd, 4th, and 5th periods of the Mendeleev periodical table, and the rare earth elements of the lanthanium and actinium series. Most of these elements are metal elements and are used in the form of oxides, fluorides, nitrides, sulfides, borides, or carbides. The chemical elements used in the method and apparatus according to the present invention for the purpose of simulating or partially simulating the bio-spectrum of the living organisms are shown in Table A.

TABLE A

| Chemical elements used in the present invention | | | | | |
|---|---|---|---|---|---|
| Monomer | | Oxides | Carbides | Nitrides | Fluorides | Borides |
| Cobalt | Co | | | | | |
| Copper | Cu | | | | | |
| Molybdenum | Mo | | | | | |
| Lithium | Li | | | | | |
| Beryllium | Be | BeO | $Be_2C$ | $Be_3N$ | | |
| Boron | B | $B_2O_3$ | $B_4C$ | BN | | |
| Magnesium | Mg | MgO | | | $MgF_2$ | |
| Aluminum | Al | $Al_2O_3$ | | | | |
| Silicon | Si | $SiO_2$ | NbC | NbN | | |
| Potassium | K | KO | | | | |
| Calcium | Ca | CaO | | | | |
| Titanium | Ti | $TiO_2$ | TiC | TiN | | $TiB_2$ |
| Vanadium | V | $V_2O_5$ | VC | VN | | $VB_2$ |
| Chromium | Cr | | $Cr_3C_2$ | CrN | | CrB ($Cr_3B_4$) |
| Manganese | Mn | $MnO_2$ | | | $MnF_2$ | |
| Iron | Fe | $Fe_2O_3$ | | | | |
| Nickel | Ni | NiO | | | | |
| Zinc | Zn | ZnO | | | ZnF | |
| Germanium | Ge | GeO | | | | |
| Strontium | Sr | SrO | | | | |
| Zirconium | Zr | $ZrO_2$ | ZrC | ZrN | | $ZrB_2$ |
| Niobium | Nb | | NbC | NbN | | $NbB_2$ |

TABLE A-continued

Chemical elements used in the present invention

| Monomer | | Oxides | Carbides | Nitrides | Fluorides | Borides |
|---|---|---|---|---|---|---|
| Tantalum | Ta | | TaC | TaN | | TaB$_2$ |
| Hafnium | Hf | HfO$_2$ | HfC | HfN | | HfB |
| Selenium | Se | | | | | |
| Thorium | Tn | TnO$_2$ | TnC | TnN | | TnB$_4$ (TnB$_6$) |
| Tungsten | W | | WcW$_2$C | | | WB |
| Cerium | Ce | CeO | | | | |
| Gold | Au | | | | | |
| Yttrium | Y | Y$_2$O$_3$ | | | | |

In the course of application of the present invention, one or a plurality of elements and their compounds can be selected from Table A according to the specific living organism to be regulated or the requirements for the simulation or partial simulation of the bio-spectrum.

The mixture ratio of the elements used in the emitting layer of the simulated bio-spectrum generator for different purposes and the applications of the apparatus according to the present invention will now be described by way of examples.

EXAMPLE 1

Treatment of AIDS

When the apparatus of the present invention is used in the treatment of AIDS, the emitting layer of the simulated bio-spectrum generator contains 16 elements mainly in the form of oxides. The mixture ration is: chromium oxide 95%, selenium oxide $\geq$1%, chromium $\geq$0.8%, geranium oxide $\geq$0.8%, zinc oxide $\geq$0.5%, ferric oxide $\geq$0.5%, magnesium oxide $\geq$0.2%, copper oxide $\geq$0.1%, cobalt oxide $\geq$0.1%, manganese oxide $\geq$0.1%, molybdenum oxide $\geq$0.1%, strontium oxide $\geq$0.1%, vanadium oxide $\geq$0.1%, aluminum oxide $\geq$0.1%, silicon oxide $\geq$0.1%, lanthanium $\geq$0.1%, magnesium fluoride $\geq$0.1%.

In treating AIDS with the apparatus so constructed, single point irradiation, localized multi-point irradiation, or general irradiation can be adopted. The principle of treatment is to prevent the onset of the disease and inhibit the antigen (HIV Ag) for patients of early infection, to increase the T cells, improve the patient's condition, and to resume immunity for patients of metaphase infection, to control the state of illness, to maintain life so as to alleviate the symptoms, and to resume physical strength for patients of late stage.

Figure 5A:
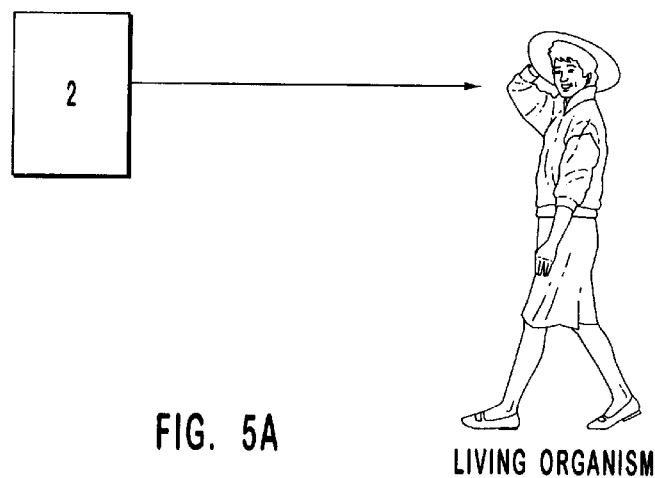
FIGS. 5A–5C are schematic diagrams showing regulation and control of the status of growth of the organisms by utilizing the apparatus according to the present invention.

The process of treatment is as follows:

(1) Local single point treatment (FIG. 5A):

Single points on chest, back, abdomen, head, feet, face, cervical vertebrae, and femur are irradiated with the apparatus containing the above elements in the emitting layer continuously for at least 5 minutes, 1–2 times a day, 30 days a course. Treatment may be conducted course by course without interruption. The therapeutic dose is controlled to the rate with which the patients feel comfortable.

Figure 5B:
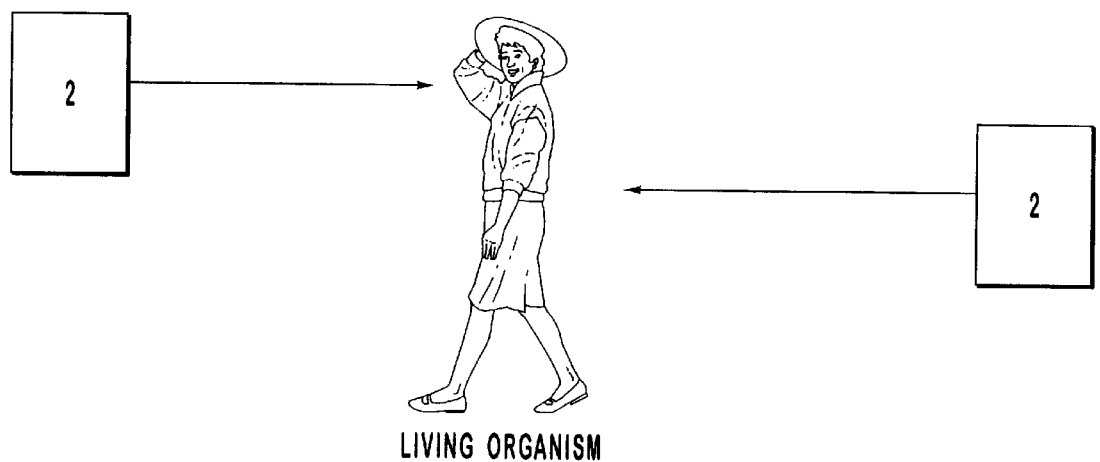

(2) Localized multi-point treatment (FIG. 5B):

Simultaneous irradiation to the thymus, spleen, stomach and intestines, vertebrae, femur, head, and feet is required in this case for at least 5 minutes at a time, 1–2 times a day, 30 days a course. There may be no interruption between courses.

Figure 5C:
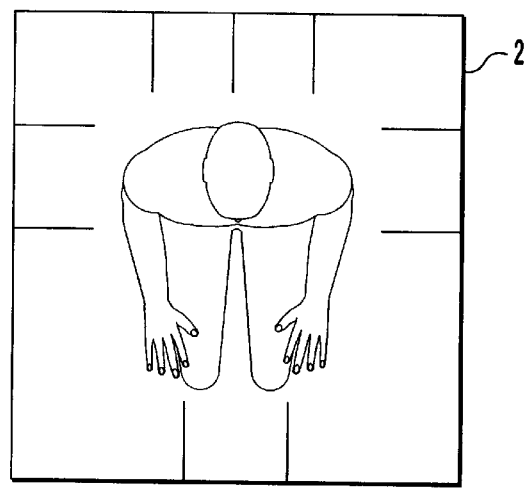

(3) General irradiation (whole body treatment) (FIG. 5C):

The whole body is irradiated for at least 5 minutes, 1–2 times a day, 30 days a course. No interruption between courses is strictly required.

(4) For patients in the exacerbation period:

The following process should be followed in addition to those described in (1), (2), and (3):

A. When accompanied with swelling of lymph nodes—irradiation should be directed to bilateral cervical, submaxillary, and inguinal lymph nodes symmetrically.

B. When accompanied with herpes—irradiation should be directed to genitalia, anus, and lip.

C. When accompanied with infection and ulcer of the anus (related to anal sexual activity)—irradiation should be directed to the lesions.

D. When accompanied by pulmonary cysticersus pneumonia (PCP)—irradiation should be directed to the lung, bronchus, and feet.

E. When accompanied by diarrhea—irradiation should be directed to the abdomen and feet.

F. When accompanied with Kaposi's sarcoma—irradiation to the lesion and the whole body is required.

G. When accompanied with perleche of the buccal cavity and tongue—irradiation to the buccal cavity and tongue, or intra-buccal cavity irradiation is required.

H. When accompanied with epilepsy—irradiation should be directed to the head and feet.

I. When accompanied with fatigue and insomnia—irradiation should be directed to the abdomen, head, and feet.

J. When accompanied with weakness of memory and headache—irradiation should be directed to head, abdomen, and feet.

In addition to the above four methods of treatment, drugs like AZT, interferon, inhibiting or regulating agents, various nutritive drugs, and medicinal herbs (Chinese medicinal herbs) may be used together with irradiation to increase the therapeutic effects or to assist the treatment.

Results of treatment of AIDS:

Twenty-five intermediate or late stage AIDS patients have been treated in accordance with the present invention. The rate of disappearance or improvement of clinical symptoms is 70%. The course of treatment is 6 months, 2 times a day. The antigen of the AIDS virus (HIV Ag) disappeared in 4 cases after treatment. For some of the patients in the early stage of infection of the virus (HIV Ag positive), HIV Ag was turned to negative after 3–6 months of treatment.

Typical case 1: a male, age 42, from New York. Before treatment: thin and fatigued with swollen lymph nodes, T4: 350, HIV Ag: 164. After two months treatment: fatigue disappeared, swelling of lymph nodes subsided, subjective feeling was well. T4: 460, HIV Ag: negative.

Typical case 2: a male from New York. Before treatment: fatigue, thin and extremely exhausted, accompanied with cysticercus pneumonia, anal herpes, and Kaposi's sarcoma, T4: 1 (normal value is 404–1700). After treatment: T4: 1, HIV Ag: not detected, fatigue relieved, cysticercus pneumonia and anal herpes disappeared, Kaposi's sarcoma of the nose subsided, body weight increased by 15 pounds.

EXAMPLE 2

Treatment of Hepatitis

When used in the treatment of hepatitis, the emitting layer of the simulated bio-spectrum generator of the apparatus according to the present invention should contain:

| | |
|---|---|
| chromium oxide 95% | ferric oxide > 0.5% |
| chromium > 0.8% | zinc oxide > 0.4% |
| copper oxide > 0.1% | cobalt oxide > 0.1% |
| manganese oxide > 0.1% | molybdenum oxide > 0.1% |
| selenium oxide > 0.7% | strontium oxide > 0.1% |
| vanadium oxide > 0.1% | aluminum oxide > 0.1% |
| magnesium oxide > 0.1% | silicon oxide > 0.1% |
| germanium oxide > 0.6% | lanthanium > 0.1% |
| boric oxide > 0.1% | magnesium fluoride > 0.1% |

The method of treatment is as follows:

When the apparatus so constructed is used to treat various types of hepatitis and cirrhosis of the liver, the irradiation is directed to the liver region, the stomach region, vertebrae, feet, and hands individually or collectively. Whole body irradiation may also be used in this case.

The course of treatment is 30 days, 1–2 times a day for 10–60 minutes. 1–7 courses are needed.

Dosage: The simulated bio-spectrum generator of the apparatus is placed 20–60 cm from the human body. It is preferable that the patient feels warm and comfortable.

Drugs like immunity regulating agents or nutritives can be used during treatment.

Effects of treatment:

Fifty cases of type B hepatitis were treated, with another 50 cases as a control group. After one month of treatment, total protein (TP) increased apparently (P<0.05), while albumin (A) increased significantly (P<0.01). The rate of relief or disappearance of clinical symptoms is 85%, serological and liver function parameters are improved, positive turning rate of HBSAg surface antigen is higher than 20%. In addition, 11 cases of cirrhosis of the liver accompanied with swelling of the spleen were treated. Albumin increased apparently (P<0.05). Type B ultrasound follow-up examination shows the spleen shrank continuously; in 4 cases, the spleen shrank to within normal range.

Mechanism of treatment of hepatitis:

Type B hepatitis is caused by the continuous duplication of HBV, which results in chronic immunological damage to liver tissue. In the early stages, the pathologic change in liver tissue is mainly degeneration of cells and inflammatory infiltration. As the change proceeds further, focal necrosis of liver cells, proliferation of fibrous tissues, damage to lobular plates, and bridge formation may occur. When the lesions develop continuously, cell necrosis and accretion will be repeated, pseudo-lobulars will be formed continuously, and portal cirrhosis of the liver will ensue. In the treatment of hepatitis using the apparatus of the present invention, the bio-spectrum acts directly on the elementary mass particles (molecules, atoms, electrons) in the liver cells to cause transitions and acquisition of energy in the liver cells. Due to the biological effects produced in the cells, organs and tissue systems by the bio-spectrum of the present invention, it is possible to stop the development of diseases effectively and in a timely fashion, to enhance biochemical metabolism and generation of normal cells, to improve circulation in the liver tissue and parameters like serum albumin, and finally to achieve the goal of treatment.

EXAMPLE 3

Treatment of Tumors

The apparatus of the present invention can be used for the treatment of many kinds of tumors. In the apparatus for the treatment of tumors, the emitting layer of the simulated bio-spectrum generator should include the following constituents:

| | |
|---|---|
| chromium oxide 93% | ferric oxide > 0.5% |
| chromium > 0.8% | zinc oxide > 0.5% |
| copper oxide > 0.1% | cobalt oxide > 0.1% |
| manganese oxide > 0.1% | molybdenum oxide > 0.1% |
| selenium oxide > 1% | strontium oxide > 0.1% |
| vanadium oxide > 0.1% | aluminum oxide > 0.1% |
| magnesium oxide > 0.1% | silicon oxide > 0.1% |
| germanium oxide > 0.1% | lanthanium > 0.1% |
| magnesium fluoride > 0.1% | |

Elements like lithium, potassium, and titanium may also be added, but the content of each of them should not exceed 0.2%.

In order to accurately confirm the therapeutic effects of the apparatus of the present invention containing the above constituents, experiments were made using cross-bred kunming mice provided by the animal center of the Chinese Academy of Medical Science as test subjects.

Cells of ascitic type liver cancer $H_{22}$ were inoculated, ascites was accumulated 48 hours later. The mice were then randomly divided into four groups and irradiated with the apparatus of the present invention containing the above constituents at a distance of 20 cm, once a day for 20 minutes. The dose way 5–30 $mw/cm^2$. The control group was injected with Pin Yang Mei Su, an anti-cancer drug produced by the Hobei Drug Manufactory, Tianjin, China, intra-peritoneally, 0.1 mg every other day.

Analysis of ascitic fluids which were randomly withdrawn 10 days later shows that in the treated mice, infiltration around the tumor cell was apparent, the number of lymphocytes increased from 22 to 41 (both B cells and T cells of the lymphocytes have anti-cancer action), and the number of cancer cells was apparently less than in those in the control group. Apparent changes in DNA content in the cancer cells of mice treated with the bio-spectrum were proved by morphmetering of the nucleus by an image analysis system, DNA multi-body determination, nucleolus surface determination, and determinations of total number and size of granules.

EXAMPLE 4

Radiation Protection

Damage caused by radiation can be protected and reduced by using the apparatus of the present invention. The emitting layer of the simulated bio-spectrum generator for this purpose should contain the following:

| | |
|---|---|
| chromium oxide 94% | ferric oxide > 0.5% |
| chromium oxide > 0.8% | zinc oxide > 0.7% |
| copper oxide > 0.2% | cobalt oxide > 0.2% |
| manganese oxide > 0.3% | molybdenum oxide > 0.1% |
| selenium oxide > 0.9% | strontium oxide > 0.1% |
| vanadium oxide > 0.1% | aluminum oxide > 0.1% |
| magnesium oxide > 0.1% | silicon oxide > 0.1% |
| germanium oxide > 0.8% | lanthanium > 0.1% |
| $CaCO_3$ > 0.1% | |

Experimentation was made on protection of animals from radiation injury using the apparatus described in this example Kunming mice, guinea pigs (serum), and sheep (whole blood) were used in the experiment. The animals were irradiated externally with -ray of $^{60}Co$ and internally with $^3$H-water-ray, then treated with the apparatus of the present invention (preventative treatment before irradiation serves the same function) twice a day for 30 minutes each time for a course of 30 days. The apparatus was placed 25 cm from the animals and the dose was controlled to 5–30 mw/cm$^2$. The results are shown in Table 1:

TABLE 1

Results of experiment with the apparatus of the present invention

| Series no. | Parameters | Reaction to Irradiation | Reaction to Irradiation plus big-spectrum (before or after irradiation) | Beneficial Effects |
|---|---|---|---|---|
| 1 | Blocks walked in open field | 100 | 130 | Increase of nerve excitability |
| 2 | Times of probing on a punched | 100 | 110 | Increase of ability of exploration |
| 3 | Avoidance of electric shock on platform | 100 | 110 | Increase of learning memory |
| 4 | Number of deformed bone marrow cells | 100 | 74 | Reduction of radiation injury |
| 5 | Slit in single chromosome | 100 | 21 | Reduction radiation injury |
| 6 | Survival of mice | 100 | 120 | Increase of survival rate |
| 7 | Number of PFC/10$^5$ spleen cells | 100 | 330 | Increase of immunologic function |
| 8 | Spleen index of mice | 100 | 130 | Increase of immunologic function |
| 9 | Rate of micro-nucleus of lymphocytes | 100 | 76 | Reduction of radiation injury |

The nine biomedical indexes in Table 1 show that the simulated bio-spectrum has anti-radiation effects or can prevent or reduce the damage from radiation.

EXAMPLE 5

Delay of Natural Degeneration of Living Organisms

The simulated bio-spectrum generator of the present invention can be used to affect the tendency of natural degeneration of living organisms when the following constituents are added:

| | |
|---|---|
| chromium oxide 94% | ferric oxide > 0.5% |
| chromium > 0.8% | zinc oxide > 0.8% |
| copper oxide > 0.2% | cobalt oxide > 0.2% |
| manganese oxide > 0.3% | molybdenum oxide > 0.1% |
| selenium oxide > 0.9% | strontium oxide > 0.1% |
| vanadium oxide > 0.1% | aluminum oxide > 0.1% |
| magnesium oxide > 0.1% | silicon oxide > 0.1% |
| germanium oxide > 0.8% | lanthanium > 0.1% |
| KI > 0.1% | BO$_2$ > 0.1% |
| CaCO$_2$ > 0.1% | MgF$_2$ > 0.1% |

To verify the effects of the present invention in this regard, mice were irradiated with said apparatus continuously for 48 days, 2 times a day, 35 minutes a time, at a dose of 5–30 mw/cm$^2$. Observation was made on the natural degeneration of the fur and the naturally swollen manubrium sterni. The results are shown in Tables 2 and 3.

TABLE 2

The effects of simulated bio-spectrum on the natural degeneration of fur in mice

| Group | Number of | Tail tip | Middle segment | Tail tip segment | Middle | Total % |
|---|---|---|---|---|---|---|
| control | 57 | 7 | 1 | 4 | 12 | 21 |
| simulated bio-spectrum | 53 | 5 | 0 | 0 | 5 | 9.4 |

The white turning rate of the fur on the tail was 21% in the control group, while only 9.4% in the bio-spectrum treated group. Hence, there is a tendency of delaying the natural degeneration.

TABLE 3

Effects of simulated-bio-spectrum on the swelling of manubrium sterni

| Group | Number of mice | Natural swelling of manubrium sterni | P-value |
|---|---|---|---|
| control | 57 | 10 (17.5%) | P < 0.001 |
| simulated bio-spectrum | 53 | 1 (1.9%) | |

In Table 3, the percentage of swelling of the manubrium sterni in the control group is 17.5%, while that of the bio-spectrum treated group is only 1.9%. P<0.001 as verified with the x test.

EXAMPLE 6

Treatment of Epilepsy

When the apparatus of the present invention is used for the treatment of epilepsy, the following constituents should be added into the simulated bio-spectrum generator:

| | | | |
|---|---|---|---|
| chromium oxide | 94% | ferric oxide | ≧0.5% |
| chromium | ≧0.8% | zinc oxide | ≧0.5% |
| copper oxide | ≧0.1% | cobalt oxide | ≧0.1% |
| manganese oxide | ≧0.1% | molybdenum oxide | ≧0.1% |
| selenium oxide | ≧0.9% | strontium oxide | ≧0.1% |
| vanadium oxide | ≧0.1% | aluminum oxide | ≧0.1% |
| magnesium oxide | ≧0.1% | silicon oxide | ≧0.1% |
| germanium oxide | ≧0.8% | lanthanium | ≧0.1% | and a small amount of metal elements such as lithium, potassium, and sodium, their total amount should not exceed 0.5%

To treat epilepsy, head, neck, feet, and hands are irradiated two times a day for 45 minutes each time for a course of 12 days. The sites to be treated must be naked and the dose is controlled to that with which the patients feel comfortable.

Mechanism of treatment and therapeutic effects:

The brain is the highest nerve center. The metabolism of the brain tissue depends strictly on the continuous supply of circulated blood to the brain. Damage to the hypothalamus by whatever reason can cause an attack of autonomic epilepsy. Epilepsy is also closely related to changes in the cerebral vessels, cerebral blood flow (CBF), and oxygen demand. Since the simulated bio-spectrum of $\mu$m to mm is acted on the brain, mainly on the hypothalamus cells, to improve its conditions, the improvement of the blood circulation in the brain and regulation of the autonomic nerves, sympathetic nerves and brain can prevent the formation of abnormal discharges of the epileptic focus. Clinical use of the apparatus for the treatment of 45 cases together with 30 cases treated with conventional drugs as the control group shows that the effective rate of a 40 day course of treatment is >90% (P<0.05) as compared with that of the control group. Abnormality rate of electro-encephalogram (EEG) of the patients is reduced by 55% after treatment, while the normal rate increased by 1.4 times. The abnormality rate of reoencephalogram (REG) of the patients is reduced by 45.72%, while the normal rate increased by 1.9 times after treatment. Recurrence occurred in all of the control cases within 7–30 days, while there had been no recurrence in the cases treated with the apparatus within six months. In addition, anxiety, nervousness, and depression were eliminated.

EXAMPLE 7

Quick Healing of Wounds and Burns

The apparatus of the present invention is applicable in accelerating the healing of various wounds and burns by adding the following constituents into the simulated bio-spectrum generator:

| chromium oxide | 95% | ferric oxide | $\geq 0.5\%$ |
|---|---|---|---|
| chromium | $\geq 0.8\%$ | zinc oxide | $\geq 0.5\%$ |
| copper oxide | $\geq 0.1\%$ | cobalt oxide | $\geq 0.1\%$ |
| manganese oxide | $\geq 0.1\%$ | molybdenum oxide | $\geq 0.1\%$ |
| selenium oxide | $\geq 0.9\%$ | strontium oxide | $\geq 0.1\%$ |
| vanadium oxide | $\geq 0.1\%$ | aluminum oxide | $\geq 0.1\%$ |
| magnesium oxide | $\geq 0.2\%$ | silicon oxide | $\geq 0.1\%$ |
| germanium oxide | $\geq 0.8\%$ | lanthanium | $\geq 0.1\%$ |

To treat various wounds and burns, the apparatus is used 1–2 times a day, 35 minutes a time. Irradiation from the apparatus is directed to the sites of treatment, i.e., opening or surface of the wounds, which should be naked and cleaned. Therapeutic effects are remarkable. In the treatment of burns, the pain is rapidly relieved; a membrane is formed, sealing the surface of the burn and the restoration stage starts immediately thereafter so that dangerous acute infections are prevented. Since it can improve microcirculation, metabolism, and regeneration of blood vessels, tissues are enhanced very significantly. As exemplified by second degree burns, the wounds of patients in the treated group were healed in four days on average (treated with the apparatus one time a day) with the wound surface being exposed completely during the treatment. While the control cases were treated with dressing changes, injections, and medications and healed in 15 days on average, accompanied with pain. At early stages of the wound, the method and apparatus according to the present invention can relieve the patients from pain rapidly, reduce exudation from the wound surface, and facilitate the generation of fiber cells, T cells, and white cells to strengthen the ability of healing. Since the circulation of body fluid is enhanced, the products of inflammation are well absorbed, and the scars formed are slight. Healing is apparently accelerated, which enables the patients to pass through the course with little anxiety or pain.

The most distinct changes of healing during treatment of wounds with the apparatus according to the invention take place on the 2nd–4th day, when the following phenomena of healing appear (incisional wound observed under microscope):

(1) WBC in superficial layer of skin changes from "distinct" to "disappeared";

(2) lymphocytes in dermis layer change from "many" to "little";

(3) fibroblasts proliferate as the healing begins, then reduce in number (representing well healed);

(4) tissue edema disappears (representing healed).

All of these phenomena appear 1–3 days earlier than in the control group.

Results of clinical experimentation on abdominal incisional wounds show that the stitches were removed after seven days with the conventional method of treatment, while stitches could be removed only four days (80–86 hours) after the operation when the apparatus is used according to the invention, and the standard of class A healing was achieved. Both pain and infection were also apparently controlled and administration of antibiotics was not needed. Body temperature returned to normal in 80 hours. Local tenderness of the wound was reduced.

EXAMPLE 8

Treatment and Prevention of Common Cold

Common cold can be treated with the apparatus described in example 7 in a manner that head, nose, buccal cavity, throat, neck, feet, and knees are irradiated 1–2 times a day, 30–120 minutes a time, for a course of 1–7 days. When used for the prevention of common cold, irradiation for three months continuously (1–2 times a day) is needed at the beginning. Then, it can be reduced to three times a week.

Therapeutic effects: At the early stage (on the day of appearance of the symptom, or Catarrh stage), the effective rate is >70% after only one time of treatment. Body temperature can be reduced to normal after two hours treatment in cases with ordinary fever. For cold at other stages, symptoms can be relieved, time of convalescence shortened, and complications prevented.

EXAMPLE 9

Treatment of Herpes

Simple herpes or herpes zoster can be treated with the apparatus described in example 7, 1–2 times a day, 40 minutes a time, for at least a course of 5 days. The sites of treatment are the lesions of the herpes, lymph nodes, feet, and spleen.

Therapeutic effects are remarkable. Painful symptoms were eliminated or relieved in 1–3 days. Blisters subsided distinctly and the rate of relapse was reduced after 1–4 courses of treatment. An effective rate higher than 90% was confirmed in 50 cases (P<0.01) as compared to the control group.

EXAMPLE 10

Treatment of Angiocardiopathy and Cerebrovascular Disease

The apparatus can be used in the treatment of angiocardiopathy and cerebrovascular disease when the following constituents are added into the simulated bio-spectrum generator:

| chromium oxide | 92% | ferric oxide | $\geq 0.5\%$ |
|---|---|---|---|
| chromium | $\geq 0.8\%$ | zinc oxide | $\geq 0.7\%$ |
| copper oxide | $\geq 0.1\%$ | cobalt oxide | $\geq 0.1\%$ |

-continued

| | | | |
|---|---|---|---|
| manganese oxide | ≧0.2% | molybdenum oxide | ≧0.1% |
| selenium oxide | ≧1% | strontium oxide | ≧0.1% |
| vanadium oxide | ≧0.1% | silicon oxide | ≧0.1% |
| germanium oxide | ≧0.1 | lanthanium | ≧0.1% |
| KI | ≧0.1% | | |

Suitable amounts (no more than 0.2%) of elements like titanium or boron are added.

In treating such diseases, irradiation is directed to the precordial region, feet, hands, vertebrae, neck, and head, 1–2 times a day, 20–60 minutes a time, for at least one course (12 days).

Therapeutic effects: Since volume of blood vessels and stroke volume of the heart are increased due to the irradiation by the apparatus, blood and oxygen supply to the heart and brain are significantly improved, which in turn improves the function of the heart and brain. Electrocardiograms and electroencephalograms are also improved. Thus, the apparatus is applicable in treating many kinds of diseases of cardiac and cerebral tissues or blood vessels. These effects are verified by animal experiments and clinical observations. It is very effective in eliminating premature beats or inverted T waves in virus myocarditis and changes of S-T segment due to coronary blood supply insufficiency. It is also capable of regulating and improving systolic conditions of the heart.

Clinical trial of the treatment of hypertension demonstrated that after 10 days treatment with the apparatus of the present invention by irradiating the underside of the foot, precordial region, hands, arms, and cervical vertebrae, systolic blood pressure dropped by 7.1% (11.4 mm Hg, P<0.002), diastolic blood pressure (DBP) dropped by 7.9% (7.9 mm Hg, P<0.001) in the treated group. The total effective rate is 54.3% (N=25). If the course of treatment is longer than 10 days, the effective rate will increase obviously and the rate of lowering of blood pressure will be higher than 80%.

Clinical trial of the treatment of coronary heart disease demonstrated that the effective rate of treatment of coronary heart disease with the apparatus is higher than 85%. Improvement in myocardial ischemia and cardiac function is apparent and statistically significant (P<0.01).

The criteria for improvement of myocardial ischemia are relief of angina pectoralis, recovery of ST-T changes, and elevation of depressed ST more than 1.0 mm.

The criteria for improvement of cardiac function are as follows: the cardiac function is lowered by one grade and reaches grade 0 or 1; the symptoms are relieved.

EXAMPLE 11

Treatment of Rheumatoid Arthritis and Other Diseases of Joints or Soft Tissues Rheumatoid arthritis can be treated with the apparatus described in example 7 in a manner that the diseased joints, spleen, femur, and feet are irradiated 1–2 times a day, 30–60 minutes a time, for 1–6 courses (20 days per course).

The treatment can be assisted by externally administered medications such as levamisole applied to the skin or the diseased joint to reinforce the therapeutic effect.

The effective rate is higher than 60%. Pain is relieved or eliminated obviously.

106 cases of lumbago (osteoarthritis, damage of the soft tissue) were treated with the present apparatus. The index of lumbago was reduced remarkably (P<0.001), while that of the control group treated with conventional medication and acupuncture showed no significant reduction (P>0.051).

EXAMPLE 12

Human Health Care

The apparatus of the present invention can be used in health care for the human body when a bio-spectrum in the micrometer wavelength range (visible light to 25 μm) is simulated. The simulated bio-spectrum generator should contain the following constituents:

| | | | |
|---|---|---|---|
| selenium oxide | ≧5% | germanium oxide | ≧5% |
| silicon oxide | ≧50% | thorium oxide | ≧4% |
| cerium oxide | ≧5% | zirconium oxide | ≧15% |
| boron nitride oxide | ≧10% | titanium carbide | ≧3% |
| tungsten carbide | ≧3% | | |

Beside, platinum 0.01% is added.

When the apparatus described in this example is used in health care for the human body, it is capable of enhancing body fluid circulation, regulating the nervous system, and strengthening psychosomatic quality. Thus, the incidence of commonly encountered diseases like the common cold are significantly reduced, digestive functions of the stomach and the intestine, sleeping, blood pressure, heart rate, and cardiac and cerebral functions are improved after three months treatment with the above method. It is particularly effective in the early stage of diseases and discomfort caused by climates, environments, psychological factors, and foods, and is capable of helping the human body to regulate and eliminate the internal changes to certain degrees, so that balance of the internal physical and chemical conditions and health of the human body are maintained.

EXAMPLE 13

Elimination of Fatigue and Enhancement of Recovery in Athletes

The apparatus of the present invention can be used to eliminate fatigue, assist recovery, and increase ability and competitive power of the professional athlete. The emitting layer of the simulated bio-spectrum generator should contain the following constituents:

| | | | |
|---|---|---|---|
| aluminum oxide | ≧85% | ferric oxide | ≧3% |
| cobalt oxide | 2% | titanium oxide | ≧3% |
| silicon oxide | 3% | hafnium oxide | ≧2% |

Besides, platinum 0.01% is added.

In eliminating fatigue in athletes and assisting recovery, the apparatus is used to irradiate undersides of the feet, abdomen, lumbar region, kidney region, or the whole body, 1–2 times a day, 30 minutes a time. It is preferable to use it after intensive exercise for the elimination of fatigue, or to use it one hour before competition for regulating psychosomatic conditions effectively.

Therapeutic effects: a 30-day trial was made on a group of 46 young or juvenile athletes (24 male and 22 female) engaged in endurance activities with daily irradiation of 30 minutes. The assigned exercise was running along a road with a slope of 150°, at a speed of 10 km/hr for six minutes. The results show that blood lactic acid levels were lower than that before irradiation, flicker fusion threshold increased, reaction time shortened, gripping force and strength of the lumbar and back muscles increased significantly.

Conclusions: the biological effects produced by the method and apparatus of the present invention function through cells receiving the effects and then casting influence on the neuro-endocrine system, especially the sympatho-adrenal system. It is capable of increasing aerobic capacity, improving the psychosomatic condition, increasing appetite and improving dream state, and therefore effective in assisting the recovery from fatigue caused by exercise, and in eliminating fatigue of central origin.

EXAMPLE 14

Treatment of Diseases of the Five Organs

The apparatus of the present invention can be used to treat diseases of the ear, nose, throat, eye, and buccal cavity when the following constituents are added into the simulated bio-spectrum generator:

| yttrium oxide | $\geq 5\%$ | ReCaMnFeOx | $\geq 90\%$ |
|---|---|---|---|
| silicon oxide | $\geq 5\%$ | | |

In treating diseases of the five organs, the treatment should be conducted 1–2 times a day, 20–40 minutes a time, for a course of 12 days. Significant effects can be obtained after 1–4 courses. The sites of treatment are mainly the sites of the lesions.

Examples of application:
Ear: otitis media, impaired hearing;
Nose: various kinds of rhinitis;
Throat: inflammation of pharynx or larynx;
Buccal Cavity: ulcers in buccal cavity;
Eyes: conjunctivitis, juvenile myopia Therapeutic effects: the effective rate of treatment of diseases of the five organs is $\geq 80\%$ on average. Impairment of circulation and nerves are eliminated timely and surgical operation can be avoided. Effective rate of treatment of juvenile pseudo-myopia is >85%.

EXAMPLE 15

Treatment of Diseases of the Kidney

The apparatus of the present invention can be used for the treatment of diseases of the kidney when the following constituents are added into the simulated bio-spectrum generator:

| chromium oxide | $\geq 96\%$ | chromium | $\geq 1\%$ |
|---|---|---|---|
| zinc oxide | $\geq 1\%$ | silicon oxide | $\geq 1\%$ |

Treatment should be conducted 1–3 times a day, 20–30 minutes a time; for a course of 30 days. The sites of treatment are the kidney region, abdomen, undersides of the feet, lumbar region, leg, or the whole body.

Therapeutic effects: in seven cases of chronic renal failure (CRF), mean BUN decreased by 32.5 mg/dl, mean urine volume increased by 255 ml/dl, hemoglobin and scr improved after treatment (P<0.05). Therapeutic effects were obtained without dialysis. The present apparatus is capable of improving the filtering and eliminating function of the renal glomeruli, and of eliminating the accumulation of metabolites of protein. Thus, diseases of the kidney are cured effectively. General post-treatment weakness and symptoms of the digestive tract are improved significantly. SOD and CGRP are also improved.

Various kinds of diseases of the kidney, including renal hypertension, can be treated with this method. It is also effective in preventing rejection after kidney transplant.

EXAMPLE 16

Treatment of Hemorrhoid

The apparatus of the present invention can be used for the treatment of hemorrhoid when the following constituents are added into the simulated bio-spectrum generator:

| titanium oxide | $\geq 90\%$ | zirconium oxide | $\geq 5\%$ |
|---|---|---|---|
| silicon oxide | $\geq 1\%$ | ferric oxide | $\geq 1.5\%$ |
| zinc oxide | $\geq 1\%$ | copper oxide | $\geq 1\%$ |
| beryllium oxide | $\geq 0.5\%$ | | |

In treating hemorrhoid, lesions at the anus are irradiated 1–2 times a day, 20–40 minutes a time, for a course of 12 days. Apparent effects were obtained in 70% of cases after one course of treatment. Undersides of feet and abdomen can be irradiated for prevention of exacerbations.

Therapeutic effects: in 64 cases of thrombosed hemorrhoid, 60 cases (93.75%) were cured substantially after one course of treatment. Inflammation and swelling subsided and pain was relieved after 2–3 times of treatment. No medication is needed during treatment. The function of improving blood circulation and regulating the nervous system performed by the present invention act on the lesion simultaneously, which accelerates the exchange of substances between blood and tissues, increases function of the reticulo-endothelial system, enhances phagocytic power of WBC, reduces muscle tone, loosens sphincter ani, and reduces tract pressure, and therefore, causes the swelling to subside in a timely fashion, leading to the thrombosed hemorrhoid being cured effectively.

EXAMPLE 17

Treatment of Menorrhalgia and Gynecologic Diseases

The apparatus of the present invention can be used to treat menorrhalgia and gynecologic diseases when the following constituents are added into the simulated bio-spectrum generator:

| silicon carbide monomer (high purity) | 90% | zinc oxide | 1% |
|---|---|---|---|
| chromium | 2% | | |
| ferric oxide | 1% | | |

When used for the treatment of menorrhalgia and gynecologic diseases (inflammation and sterility), the apparatus of the present example is operated to irradiate the sites of treatment 1–2 times a day, 20–40 minutes a time. A course of treatment for menorrhalgia contains seven treatments; while a course of treatment for other gynecologic diseases contains 30 treatments.

The sites of treatment are the sites of pain and inflammation, abdomen, lumbar region, perineal region, and undersides of the feet.

Therapeutic effects: in 79 cases of menorrhalgia, 65 cases (82.3%) were cured and obvious effects were obtained in 10 cases (12.7%).

Among 52 cases of inflammation of the pelvic cavity and its appendix tested, 14 were cured, 36 improved, and 2 were ineffective. The effective rate is higher than 90%. The period of treatment needed was 20 days on average.

15 cases of erosion of the cervix uteri were tested, 5 cured, 9 improved, and no effect in 1 case. The period of treatment was 10 days on average.

It is also effective for treatment of sterility, but the observation is not completed yet.

EXAMPLE 18

Treatment of Respiratory Diseases

The present invention can be used for the treatment of respiratory diseases when the following constituents are added into the simulated bio-spectrum generator:

| ferric oxide | ≧20% | zirconium oxide | ≧75% |
|---|---|---|---|
| silicon oxide | ≧2% | zinc oxide | ≧1% |
| niobium oxide | ≧2% | | |

When used for the treatment of respiratory diseases, the apparatus should act on the patients 1–3 times a day, 20–40 minutes a time, for a course of 30 days.

Sites of treatment: bronchus, chest, undersides of the feet, preferably the chest and back at the same time.

Therapeutic effects: good anti-asthmatic effects can be obtained in treating bronchial asthma. When chronic asthmatic bronchitis cases accompanied with emphysema are treated for three courses, the asthmatic symptoms can be relieved. Preventive results can be achieved for respiratory bronchial asthma.

Cases of acute bronchitis and pneumonia are cured after 7.7 days (average) of treatment, while the control group cured after 9.05 days. The difference is significant ($P<0.05$).

The mechanism of suppressing the asthma and eliminating inflammation is to increase non-specific immunologic mechanism and anti-allergic action, regulate and balance autonomic nervous functions, reduce excitability of the sympathetic nerves, stop cough and sputum, suppress asthma. The apparatus has an anti-infectious function and is capable of suppressing asthma immediately. It is also effective for emphysema or cor pulmonale.

Effectiveness in treatment of respiratory diseases can be enhanced by accompaniment of medications.

EXAMPLE 19

Treatment of Diseases of the Stomach and the Intestine

The apparatus of example 18 can also be used for the treatment of diseases of the stomach and the intestine. The treatment should be conducted 1–3 times a day, 20–40 minutes a time. The course of treatment for diseases of the intestine is seven days.

Sites of treatment are the gastric and intestinal regions, knee joints, and undersides of the feet.

Therapeutic effects: gastric ulcer and gastritis treated for one course, effective rate ≧90%. Chronic gastritis treated for one course, effective rate ≧90%.

No medication is needed during treatment. It is also effective in treating diseases relating to insufficient enzyme for digestion of milk in the stomach.

EXAMPLE 20

Enhancing Hair Growth

The apparatus of the present invention can be used for enhancing hair growth when the following constituents are added into the simulated bio-spectrum generator:

| silicon oxide | ≧80% | ferric oxide | ≧2% |
|---|---|---|---|
| vanadium oxide | ≧2% | zinc oxide | ≧2% |
| titanium oxide | ≧2% | boron nitride | ≧2% |
| tungsten carbide | ≧1% | magnesium oxide | ≧2% |
| calcium oxide | ≧5% | cerium oxide | ≧2% |

The method of using this apparatus for the treatment of baldness and enhancement of hair growth is as follows: daily irradiation, 1–2 times, 20–30 minutes a time, is directed for at least one course of 30 days to sites of alopecia over the head, undersides of the feet, abdomen, lumbar and kidney regions. This apparatus can be used alone or accompanied prior to irradiation with local lotion medications that enhance blood circulation in the skin of the scalp, and stimulate hair growth.

Therapeutic effects: this apparatus is mainly used for treating alopecia seborrhoeica. It regulates endocrine secretion, enhances metabolism, increases skin respiration, so that the subsided growth information and growth of hair roots can be restored.

It is also effective for other kinds of alopecia or even poliosis owing to its anti-senescent function (please refer to example 5).

EXAMPLE 21

Treatment of Chloasma

The apparatus of example 19 can be used for treating chloasma in a way that irradiation is directed to the face, umbilicus, abdomen, kidney region, undersides of the feet, and head one time a day, 20–30 minutes a time, for a course of 30 days.

When skin-protecting lotions or cosmetic measures are used, the facial region can be irradiated with the apparatus before or after the cosmetic measures. Umbilicus, abdomen, kidney region, undersides of the feet, and head can also be irradiated at the same time. It is capable of accelerating the absorption of nutritive substances by the skin and improving blood supply and respiration of the skin locally, while regulating the endocrine system and eliminating impairment of circulation or nervous activities in the whole body, so as to remove the fundamental cause of chloasma internally through the organs, tissues, and the nervous system.

The apparatus of this example can be used for cosmetics and health care. The effects are achieved through the improvement of general physical conditions and prevention of senescence fundamentally.

EXAMPLE 22

Application in the Simulation of Bio-Informations

Certain informations of the living organism can be simulated with the present invention. For example, body temperature, pulse, heart rate, and the frequency, amplitude, or wave form of bio-physical parameters like ECG or EEG can be simulated by means of various apparatus for the purposes of training and induction, as well as treatment and health care of patients.

EXAMPLE 22-1

Application in the Simulation of Information of Chinese "Qi-Gong" and Indian "Yoga"

It is known from recent studies and measurements that information of Chinese "Qi-Gong" and Indian "Yoga" is in the spectral range of μm–mm. However, the changes and fluctuations of information emitted by those who are practicing Qi-Gong or Yoga are different. According to the results of these studies, the apparatus of the present invention is capable of simulating information of Chinese "Qi-Gong" and Indian "Yoga". This kind of apparatus will help train or induce the beginners, or will help the well-trained to enter the practicing state in non-quiet environments by simulating Qi-Gong or Yoga information. When the apparatus of the present invention is used to simulate Qi-Gong or Yoga information, the emitting layer of the simulated bio-spectrum generator should contain:

| aluminum oxide | ≧85% | cerium oxide | ≧1% |
| --- | --- | --- | --- |
| ferric oxide | ≧5% | cobalt oxide | ≧3% |
| chromium oxide | ≧5% | silicon oxide | ≧1% |

When the apparatus is supplied with electrical power that pulsates at a frequency of 0–60 cycles/minute, the spectral information generated approaches that of Qi-Gong or Yoga, and can perform the function of training and health care.

Signals at a broad band or a single frequency within the range of μm–mm, when changed both in amplitude and frequency, will act like the information of Qi-Gong or Yoga.

EXAMPLE 22-2

According to the principle of the present invention and by using the apparatus of the present invention, the range of the spectrum is restricted to 0.6–30 μm. In this case, the simulated bio-spectrum generator contains magnesium fluoride ($MgF_2$) in 100%.

The simulated bio-spectrum of the apparatus of the present invention can also be made to contain mainly magnesium fluoride (50%), the other constituents can be materials with high chromaticity, high rate of radiation, and broad comprehensive spectrum. In this example, the are:

| magnesium fluoride ($MgF_2$) | ≧50% | titanium oxide ($TiO_2$) | ≧5% |
| --- | --- | --- | --- |
| nickel oxide (NiO) | ≧5% | tin oxide ($SnO_2$) | ≧1% |
| manganese oxide ($MnO_2$) | ≧6% | (BN) | ≧20% |

This apparatus is powered intermittently with a power source which works two seconds in every 10 seconds, so that a changing spectrum is generated.

EXAMPLE 23

Application in Animals

The present apparatus is capable of enhancing the growth and development of animals, increasing hatchability of eggs, improving the quality of semen, treating various diseases of animals, and helping prolong the survival period of rare animals when the following constituents are added into the simulated bio-spectrum generator:

| chromium oxide | 90% | ferric oxide | ≧1% |
| --- | --- | --- | --- |
| chromium | ≧1% | zinc oxide | ≧1% |
| copper oxide | ≧0.2% | cobalt oxide | ≧0.2% |
| manganese oxide | ≧0.5% | molybdenum oxide | ≧0.1% |
| selenium oxide | ≧1.5% | strontium oxide | ≧0.1% |
| vanadium oxide | ≧0.1% | aluminum oxide | ≧0.2% |
| magnesium oxide | ≧0.8% | silicon oxide | ≧0.3% |
| germanium oxide | ≧1% | lanthanium | ≧0.1% |
| KI | ≧0.1% | | |

1. When this apparatus is used to irradiate the perineal and testis region of stud stock once a day for 20–60 minutes with a surface power of 5–30 mw/cm² for 20 days, sperm activity is increased by 10–20%, sperm density by 5–14%, activity after freezing by 50%. Qualified semen can be increased by over three times and fertility rate is also increased significantly. The effect on the development of the fetus is apparent.

2. When this apparatus is used to irradiate chickens, 30–300 minutes a day, with the skin temperature of the chicken being controlled at 31°–37° C. continuously or intermittently, body weight of 30-day chickens is increased and diarrhea of chickens is prevented effectively.

3. When the apparatus is used to irradiate stud eggs, the hatching rate is increased. For this purpose, the eggs are fixed first, irradiation is directed thereto for 30–50 minutes, the surface temperature of the eggs is controlled to 36°–37° C. The process is repeated once a day for 1–6 days. 1–3 times more irradiation before breaking of the shell can increase the hatching rate by 5–20% and can shift the time of outburst to 3–20 hours earlier than usual.

4. Application in the treatment of mastitis in cows is confirmed by irradiating the breast of the cow, 30–50 minutes, 1–2 times a day, for a course of five days or more. After treatment, infections can be controlled, inflammation can be eliminated, and milk production restored.

5. Application in the treatment of gastroenteritis of animals has been proven. Irradiation should be directed to the region of the stomach and intestine, 30–60 minutes a time, 1–3 times a day for a course of five days or more. After treatment, inflammation can be eliminated and toxic substances in the gastroenteric tract can be neutralized. Gastroenteric functions are thus restored.

6. The apparatus can be used to treat trauma such as hematoma or sprain of joints. Irradiation to the sites of trauma or sprain, 20–40 minutes a time, 1–2 times a day, for a least a course of four days, can eliminate hematoma, has the products of inflammation absorbed, and reduces sensitivity of the trauma and enhances regeneration and restoration.

EXAMPLE 24

Applications in Plants

The apparatus of example 22 is capable of influencing the status of growth of plants, but small amounts of potassium, phosphorus, and nitrogen (each kind no more than 0.5%) must be added into the emitting layer of the simulated bio-spectrum generator and the ratio of ultraviolet light and visible light in the radiation should also be increased. In this case, the ultraviolet rays can be obtained from a separate source, while the visible light is generated by the present invention itself.

The purpose of the application of the present apparatus in plants is:

1. To increase the resistance to adverse conditions, to increase cold resistance, drought resistance, and disease resistance, to improve quality, and to modify variety;

2. To increase the rate of germination;

3. To shorten the period of growth of economic crops, to facilitate early ripening, and to increase production and benefits;

4. To influence gene formation, to breed new varieties, and to alter the form and color of plants.

Taking seeds as an example: when seeds are germinating, the starch in the endosperm is decomposed into monosaccharides and transported to the embryonic organs. Starch is hydrolyzed into maltose by -amylase and -amylase, then decomposed into glucose by maltase to provide substances and energy for the growth of the embryo. The activity of amylase has direct influence on germination of the seeds and growth of the seedlings. The method and apparatus of the present invention are capable of increasing the total amylase by 100% more than the control group. The activities of peptidase, ascorbic acid oxidase, nitrate reductase, and lipoproteinase are also increased. Seedling respiration is increased after treatment of the seeds.

A. When tobacco seedlings were irradiated with the above mentioned apparatus once a day, 40 minutes at time, for three consecutive days form a distance of 40—40 cm and with a surface intensity of 0.1–0.25 mw/cm$^2$, irradiated tobacco seedlings became resistant to the tobacco mosaic virus, their resistance to adverse conditions increased, and yield also increased.

B. Dry seeds of paddy rice were irradiated with the apparatus within 60 days before sowing under the following conditions: thickness of rice seeds was 1–1.5 cm; the simulated bio-spectrum generator was placed 25–60 cm away form the seeds; duration of irradiation was 40–150 minutes preferably 100 minutes; surface temperature of the seeds was controlled to 41°–49° C. After irradiation, rooting ability, tillering ability, shooting ability, drought resistance, disease resistance, and quality of the seedlings were all increased. Yield of rice was also increased.

The apparatus of the present invention can be widely applied to seedling culture and seed treatment in agriculture, forestry, and gardening.

EXAMPLE 25

Application in Microorganisms

The importance of genes to living organisms led to the development of bio-technology and gene engineering. The present invention will help bio-technology and gene engineering directly or indirectly in the following aspects:

1. Irradiation of fungi with the apparatus of example 24, 1–3 irradiations at a dose of 10–2 mw/cm$^2$ for 30 minutes can be made on stock plants, original seeds, or cultigens. It can increase functions of the hypha, decompose and absorb nutrients in the matrix, and differentiate fruiting bodies. As compared with the control group, there are tendencies to increase reproductivity, shorten the period of growth, and increase yield.

2. Irradiation with the apparatus of example 24 can increase the yield and quality of antibiotics. When the simulated bio-spectrum is used to irradiate the cultures, the irradiation should be made with an intensity of 5–20 mw/cm$^2$ and at a temperature of 27°–30° C., 1–3 times, 40 minutes a time. Penicillin can be irradiated during the course of production for 40 minutes, the dose is 5–10 mw/cm$^2$, with ambient temperature of 25°–27° C. and pH value of 6.8–7.2.

The present invention shows a tendency to improve the respiration of the microorganism, and to make the absorption and transformation of oxygen reach the utmost degree of metabolic activity. It can also be used to increase the quality of brewing.

EXAMPLE 25-1

Direct Action on DNA

Erroneous connection of chromosomes, arrangement and amount of DNA can cause handicaps and diseases such as tumors or Down's syndrome in human beings. The apparatus can perform the function of directly repairing and regulating DNA which is conducive to the relief of diseases. The emitting layer should contain the following compounds:

| chromium oxide | $\geq 80\%$ | beryllium oxide | $\geq 1\%$ |
|---|---|---|---|
| copper oxide | $\geq 2\%$ | zinc oxide | $\geq 3\%$ |
| cobalt oxide | $\geq 2\%$ | niobium oxide | $\geq 1\%$ |
| calcium oxide | $\geq 3\%$ | strontium oxide | $\geq 1\%$ |
| silicon oxide | $\geq 2\%$ | selenium oxide | $\geq 2\%$ |
| molybdenum oxide | $\geq 1\%$ | ferric oxide | $\geq 2\%$ |

EXAMPLE 25-2

Enhancement of Microbiologic Drug Manufacturing

The apparatus of example 25-1 can help in synthesizing insulin by DNA recombination techniques. The genes that produce insulin are first isolated from the nucleus of a human cell and cut down with restriction enzyme. Then, the plasmid in bacteria is also cut down and combined with the genes that produce insulin. The new combination is then put back into the bacteria, and the bacteria are put into a fermentation tank to propagate, and hence, produce insulin. When the present invention is used to irradiate the bacteria directly, or to make a bio-spectrum fermentation tank, the rate of successful DNA recombination, transplantation, and bacterial propagation can be increased, leading to the increase of insulin yield. This method can also be applied to synthesizing hormones and antibiotics.

EXAMPLE 25-3

Construction of New Organic Tissue

When the gene recombination transplantation technique assisted by the apparatus of example 25-1 is applied to plants or animals, the speed of growth is accelerated, fruits of crops become larger, the crops are cold, pest, and drought resistant, the body weight and disease resistance of animals are increased. When using the present invention, the rate of successful gene recombination transplantation in plants or animals is increased because the present invention is capable of influencing the arrangement and amount of DNA. The method of the present invention can be used to directly irradiate the cells of embryos after recombination of the genes.

EXAMPLE 26

Plastics and Textiles Which Can Radiate Simulated Bio-Spectrum

In order for the present invention to be applied widely, one or more monomers or compounds of chemical elements which can generate simulated bio-spectrum can be mixed with raw materials to make various kinds of plastics or textiles. The constituents that should be added are as follows:

| zinc oxide | $\geq 5\%$ | ferric oxide | $\geq 3\%$ |
|---|---|---|---|
| silicon oxide | $\geq 5\%$ | germanium oxide | $\geq 10\%$ |
| thorium oxide | $\geq 2\%$ | chromium oxide | $\geq 75\%$ |

The chemical elements of this example can be mixed into the raw material of plastics directly, into paints, dyes, enamels, or other coating materials which will be painted onto the surface of the plastic products. They can also be mixed into the textiles (cloth, artificial leather) to form a radiating surface membrane.

The plastics or textiles which can radiate simulated bio-spectrum can be used for health care in humans or animals, for crop breeding or seedling nursing, as well as for microbiologic fermentation. The applications of the materials using different sources of energy are now described.

1. Electricity as energy source

Electric wires of certain resistance are embedded into plastics or textiles that contain the simulated bio-spectrum generating substances as described in example 26. The electric wires are designed to have certain heat generating power and cross sectional areas like that used in electric heating blankets. When being heated by electricity, this kind of plastic or textile can generate simulated bio-spectrum of certain intensity, which can enhance body fluid circulation and improve the function of the nervous system. It is beneficial to health when used for a long period of time. This kind of material can be made into electric heating blankets, local health bands, chair cushions for offices, cars, boats, or airplanes, mattresses, beds for home use, and sporting goods. The heating temperature is controlled below 45° C.

2. Magnetic field as energy source

Magnetic material can be added into the plastic or textile containing substances that generate the simulated bio-spectrum as described in example 26. The magnetic material can be various kinds of permanent magnets. Under the action of the magnetic field, the simulated bio-spectrum generated by the plastic or textile can be intensified. The dual action of the spectrum and the magnetic field can enhance body fluid circulation and health care. This example can be used to make various kinds of mattresses or chair cushions, hats, shoes, waist or knee bands, or to wrap strong magnetic materials to make various kinds of magneto-spectral health care equipment.

3. Solar energy as heating energy

Plastics or textiles, including plastic membranes, containing the simulated bio-spectrum generating substances as described in example 26 can be used to make large tents or rooms so that the plastics or textiles can be heated by solar energy and become the simulated bio-spectrum generator. This example can be used for seedling nursing, breeding, or low temperature culturing.

4. Body heat or ambient heat as energy source

The plastics or textiles containing simulated bio-spectrum generating substances as described in example 26 can be used to make articles for daily use such as shoes, caps, waist bands, mattresses or cushions, so that heat produced by the human body or natural heat from the environment can act as the energy source. Long term contact with such articles will assist blood circulation and heat preservation.

The chemical constituents contained in the simulated bio-spectrum generator of the present invention have been described by way of examples. In practical use, these chemical constituents can be adjusted appropriately. For example, the oxides can be substituted with fluorides, carbides, or nitrites. The mixture ratio of these constituents can also be readjusted, but at least one or a few of the elements in Table 1 or their compounds should be contained. When any one of the following elements or its compounds serves as the main constituent, it should account for no less than 50%: chromium, magnesium, selenium, germanium, zinc, copper, aluminum, strontium, cerium, yttrium, calcium, zirconium, molybdenum, silicon, iron, vanadium.

The simulated bio-frequency spectrum generator of the present invention can also contain the radiation source of gray body or near black body which consists of a plurality of ceramics, metals, or the combination of ceramics and metals.

The principle of determining the proportions of the above chemical constituents or determining the radiation sources of the gray or near black body mentioned above is that their spectrum should be as similar to the spectrum of the subject organism as possible. That is to say, the simulated bio-spectrum should overlap with the bio-spectrum; the more the overlap, the better. For complicated organisms such as human beings or animals, the spectrum to be simulated with the constituents in certain proportions should be as broad as possible. It is preferable to cover ultraviolet, visible light, infrared through millimeter waves, so that sufficient transitions of the molecules, atoms and electrons can be elicited simultaneously.

The applicant finds whatever the proportions of the chemical elements may be, the key point is whether the spectral signal generated by the simulated bio-spectrum generator and the energy elicited by the electrons or the excited molecules can be utilized to achieve biological effects of beneficial regulation. A spectral range of 0.2 $\mu$m–10 cm covers most of the bio-spectrum. A means for effectively adjusting and improving the development and survival of living organisms is provided through the application of the method and apparatus of the present invention. Many kinds of diseases can be treated with the apparatus of the present invention.

TABLE B

Functions and Therapeutic Effects of the Apparatus of the Present Invention

| Diseases | sites of treatment | Min./ time | times/ day | days/ course | therapeutic effects |
|---|---|---|---|---|---|
| common cold | face, vertebrae, undersides of feet | 20–60 | 1–4 | 1–6 | early stage: good; middle or late stage: fair effective rate ≧70% |
| German measles | lesion | 20–40 | 1–4 | 1–10 | relief of itching ≧70% |
| hepatitis | liver region, back, undersides of feet | 20–60 | 1–3 | 30–15 | effective rate ≧80% |
| dysentery | abdomen, | 20–50 | 1–4 | 1–10 | e.r. ≧80% |

TABLE B-continued

Functions and Therapeutic Effects of the Apparatus of the Present Invention

| Diseases | sites of treatment | Min./ time | times/ day | days/ course | therapeutic effects |
|---|---|---|---|---|---|
| acute or chronic bronchitis | undersides of feet lungs, bronchus, back | 20–60 | 1–2 | 3–30 | e.r. ≧60% |
| asthma | lungs, bronchus, back | 20–60 | 1–3 | 30–90 | e.r. ≧60% |
| pneumonia | lungs, bronchus, back | 20–60 | 1–3 | 2–7 | e.r. ≧80% |
| rheumatic fever | lungs, bronchus, back | 20–50 | 1–2 | 10–20 | remission rate ≧40% |
| rheumatic heart disease | chest, joint | 20–50 | 1–2 | 10–60 | r.r. ≧60% |
| hypertension | chest, vertebra, head, undersides of feet | 20–40 | 1–2 | 30 | effective rate ≧90% |
| coronary heart disease | chest, head, feet | 20–40 | 1–2 | 30 | e.r. ≧90% |
| viral myocarditis | chest, head, feet | 20–40 | 1–2 | 30 | e.r. ≧85% |
| Raynaud's disease | chest, head, feet | 20–40 | 1–2 | 30 | e.r. ≧70% |
| arrhythmia | chest, head, feet | 20–40 | 1–2 | 5–30 | e.r. ≧70% |
| heart failure | chest, head, feet | 20–40 | 1–2 | 5–30 | e.r. ≧80% |
| acute and chronic gastritis | gastric region, abdomen | 20–40 | 1–2 | 5–30 | e.r. ≧85% |
| peptic ulcer | gastric region, abdomen | 20–40 | 1–2 | 30 | e.r. ≧90% |
| chronic colitis | gastric region, abdomen | 20–40 | 1–2 | 30 | e.r. ≧90% |
| cirrhosis of liver | liver, abdomen, back, feet | 20–40 | 1–3 | 30 | e.r. ≧70% |
| acute and chronic pancreatitis | lesion, abdomen, lumbar region | 20–40 | 1–3 | 2–30 | e.r. ≧65% |
| gastroenteric neurosis | stomach, abdomen, undersides of feet | 20–60 | 1–3 | 3–30 | e.r. ≧70% |
| leukemia | whole body, chest, spleen, abdomen, vertebra, feet | 20–60 | 1–3 | 30–90 | e.r. ≧30% |
| diabetes | region of islets of Langerhans abdomen, lumbar region, feet | 20–60 | 1–3 | 3–90 | e.r. ≧60% |
| disturbance of acid base equilibrium | chest, abdomen, vertebra, feet | 20–60 | 1–3 | 5–30 | e.r. ≧60% |
| obesity | abdomen, back, feet | 20–60 | 1–3 | 30 | remission rate ≧60% |
| malnutrition | abdomen, stomach, kidney region, feet | 20–60 | 1–3 | 5–30 | r.r. ≧50% |
| beri-beri | lesion | 20–60 | 1–3 | 7–30 | r.r. ≧60% |
| nephrosis syndrome | kidney region, feet, abdomen, whole body | 20–60 | 1–3 | 30 | r.r. ≧75% |
| uremia | kidney region, feet, abdomen, whole body | 20–60 | 1–3 | 30 | r.r. ≧60% |
| alcoholism | liver, abdomen, stomach, whole body | 20–60 | 1–3 | 5–30 | effective rate ≧65% |
| narcotics abstinence | head, feet abdomen, stomach, whole body | 20–60 | 1 | 30 | e.r. ≧65% |
| food poisoning | liver, abdomen, stomach, whole body | 60 | 1–3 | 1–7 | e.r. ≧70% |
| remission of radiation | whole body | 60 | 1–2 | 30 | e.r. ≧65% |

TABLE B-continued

Functions and Therapeutic Effects of the Apparatus of the Present Invention

| Diseases | sites of treatment | Min./ time | times/ day | days/ course | therapeutic effects |
|---|---|---|---|---|---|
| sickness intensification of anesthesia | site of injection of anesthetics | 5–20 | 1 | 1 | e.r. ≧70% |
| sedation | head, feet abdomen | 20–60 | 1–2 | 1–10 | e.r. ≧80% |
| hypnogenesis | head, feet, stomach, abdomen | 20–50 | 1 | 30 | e.r. ≧70% |
| analgesia | lesion | 20–60 | 1–3 | 30 | e.r. ≧80% |
| closed wound | wound | 20–40 | 1–2 | 2–10 | e.r. ≧85% |
| open wound | wound | 20–40 | 1–3 | 2–10 | e.r. ≧90% |
| quick healing of surgical wound | wound | 20–40 | 1–3 | 3–5 | e.r. ≧90% |
| burns | lesion | 20–40 | 1–3 | 3–5 | e.r. ≧90% |
| frostbite | lesion | 20–40 | 1–3 | 3–5 | e.r. ≧90% |
| poisonous snake bite | lesion | 60 | 1–3 | 10 | e.r. ≧80% |
| pyemia | lesion | 30–S0 | 1–3 | 10 | e.r. ≧80% |
| furuncle | lesion | 30–50 | 1–3 | 3–10 | e.r. ≧80% |
| carbuncle | lesion | 30–50 | 1–3 | 3–10 | e.r. ≧85% |
| cellulitis | lesion | 30–50 | 1–3 | 3–10 | e.r. ≧85% |
| lymphangitis | lesion | 30–50 | 1–3 | 3–10 | e.r. ≧85% |
| erysipelas | lesion | 30–50 | 1–3 | 3–10 | e.r. ≧85% |
| paronychia | lesion | 30–50 | 1–3 | 2–8 | e.r. ≧85% |
| peritendinitis | lesion | 30–50 | 1–2 | 30 | e.r. ≧60% |
| bone tumors | whole body lesion, with healing of surgical wound | 20–60 | 1–3 | 5–30 | - remission |
| damage of peripheral nerves | lesion | 20–40 | 1–3 | 10–30 | effective rate ≧60% |
| difficulty in urination | perineum, abdomen, kidney region | 20–40 | 1–3 | 5–20 | e.r. ≧60% |
| retention of urine | perinium, abdomen, kidney region | 20–40 | 1–3 | 5–20 | e.r. ≧60% |
| swelling of scrotum | lesion | 20–40 | 1–3 | 5–30 | e.r. ≧60% |
| cystitis | perinium, bladder | 20–40 | 1–3 | 5–30 | e.r. ≧70% |
| prostatitis | perinium, lower abdomen | 20–40 | 1–3 | 5–30 | e.r. ≧80% |
| renal hypertension | kidney region, feet, whole body | 20–40 | 1–3 | 30–60 | e.r. ≧80% |
| anti-inflammation and analgesia of gall stone and kidney stone | lesion | 20–40 | 1–3 | 3–15 | remission |
| infertility or sterility | whole body, perinium, abdomen, uterus, feet, vertebrae | 20–40 | 1–3 | 5–30 | effective rate ≧60% |
| disturbance in sexual function | whole body, perinium, | 20–40 | 1–3 | 5–30 | e.r. ≧60% |
| care of premature infant | whole body | 15–60 | 1–3 | 3–20 | e.r. ≧60% |
| hepatitis accompanied by pregnancy | whole body, liver region, feet | 20–40 | 1–2 | 20–80 | e.r. ≧60% |
| puerpural infection | lesion | 20–40 | 1–3 | 5–15 | e.r. ≧70% |
| cervicitis | lesion | 20–40 | 1–3 | 30 | e.r. ≧85% |
| vaginitis | lesion | 20–40 | 1–3 | 5–30 | e.r. ≧85% |
| pelvic infection | perinium | 20–40 | 1–3 | 30 | e.r. ≧85% |
| metropathia hemorrhagica | perinium, uterine projection area | 20–40 | 1–3 | 30 | remission |
| lactation menopause syndrome | lesion, feet, abdomen | 20–40 | 1–3 | 5–30 | effective rate ≧70% |
| premenstrual | abdomen, | 20–40 | 1–3 | 5–30 | e.r. ≧90% |

TABLE B-continued

Functions and Therapeutic Effects of the Apparatus of the Present Invention

| Diseases | sites of treatment | Min./ time | times/ day | days/ course | therapeutic effects |
|---|---|---|---|---|---|
| anxiety | feet | | | | |
| climateric syndrome | whole body | 20–40 | 1–3 | 30 | e.r. ≧45% |
| menopause | whole body, abdomen | 20–40 | 1–3 | 30 | e.r. ≧50% |
| menorrhalgia | abdomen | 20–40 | 1–3 | 30 | e.r. ≧50% |
| breast tumor | lesion, whole body | 30–60 | 1–2 | 30 | remission |
| gas gangrene | lesion | 40 | 1–3 | 10 | remission |
| mastitis | lesion | 30–50 | 1–2 | 2–10 | effective rate ≧70% |
| proliferation of lobuli mammae | lesion | 30–50 | 1–2 | 30 | e.r. ≧70% |
| hernia | lesion | 30–50 | 1–2 | 30 | e.r. ≧60% |
| peritonitis | lesion | 30–50 | 1–2 | 30 | e.r. ≧70% |
| fistula or abscess of anus or intestine | lesion | 30–50 | 1–2 | 30 | e.r. ≧90% |
| fissure ani | lesion | 30–50 | 1–2 | 2–20 | e.r. ≧90% |
| hemorrhoid | lesion | 30–50 | 1–2 | 2–20 | e.r. ≧90% |
| cholecystitis | lesion | 30–50 | 1–2 | 2–20 | e.r. ≧70% |
| angiitis | lesion | 30–50 | 1–2 | 30 | e.r. ≧30% |
| varicose of vein of lower extremity | lesion | 30–50 | 1–2 | 30 | remission |
| chronic ulcus cruris | lesion | 30–50 | 1–2 | 30 | effective rate ≧80% |
| quick healing of plastic operation | lesion | 20–40 | 1–2 | 2–7 | e.r. ≧95% |
| elimination of repelling reaction | lesion | 20–60 | 1–3 | 2–10 | e.r. ≧95% |
| quick healing of fracture | lesion | 20–60 | 1–3 | 2–10 | e.r. ≧85% |
| damage of meniscus | lesion | 20–60 | 1–3 | 5–20 | e.r. ≧75% |
| enhancement of healing of replantation of extremities | lesion | 20–60 | 1–3 | 3–10 | e.r. ≧95% |
| purulent osteomyelitis | lesion | 20–60 | 1–3 | 20–40 | e.r. ≧80% |
| rheumatoid arthritis | lesion | 20–60 | 1–3 | 30–60 | e.r. ≧80% |
| arthritis | lesion | 20–60 | 1–3 | 30–60 | e.r. ≧90% |
| osteoporosis | lesion, whole body | 20–60 | 1–3 | 30–60 | e.r. ≧70% |
| sequelae | lesion | 20–60 | 1–3 | 30–60 | remission |
| pain in neck, shoulder, or lumbar region | lesion | 20–60 | 1–3 | 3–30 | effective rate ≧95% |
| periarthritis of shoulder joint | lesion | 20–60 | 1–3 | 3–30 | e.r. ≧95% |
| epichondylitis of humerus | lesion | 20–60 | 1–3 | 3–30 | e.r. ≧95% |
| vomiting of infant | stomach, abdomen | 15–20 | 1–2 | 5 | e.r. ≧90% |
| scleroderma neonatorum | abdomen, perineum | 15–20 | 1–2 | 5 | e.r. ≧90% |
| subcutaneous gangrene of newborn infant | lesion | 15–20 | 1–2 | 7 | e.r. ≧80% |
| septicemia of newborn infant | whole body | 15–20 | 1–2 | 7 | remission |
| tetanus of newborn infant | whole body | 15–30 | 1–2 | 10 | remission |
| hemolysis of newborn infant | whole body | 15–30 | 1–2 | 10 | remission |
| infantile diarrhea | abdomen | 15–30 | 1–2 | 2–7 | effective rate ≧90% |
| inflammation infant buccal | inside or outside of | 15–20 | 1 | 2–10 | e.r. ≧70% |

TABLE B-continued

Functions and Therapeutic Effects of the Apparatus of the Present Invention

| Diseases | sites of treatment | Min./ time | times/ day | days/ course | therapeutic effects |
|---|---|---|---|---|---|
| cavity | lesion | | | | |
| acute respiratory infection of infant | chest, accompanied with medication | 15–20 | 1 | 3–7 | e.r. ≧95% |
| infantile pneumonia | chest, accompanied with medication | 15–20 | 1 | 3–7 | e.r. ≧95% |
| infantile nephrosis | kidney region, feet, whole body | 15–30 | 1 | 10 | e.r. ≧85% |
| infantile tuberculosis | chest, spleen region, feet | 15–30 | 1 | 20 | e.r. ≧70% |
| mild disturbance of cerebral function of infant | head, feet, vertebrae | 15–30 | 1 | 20 | e.r. ≧70% |
| incontinence of urine | perineum, lumbar and kidney region | 15–30 | 1–2 | 3–7 | e.r. ≧95% |
| immunodeficiency | whole body | 15–30 | 1–2 | 20 | remission |
| paralysis | whole body | 60 | 1–2 | 30 | remission |
| facial neuritis | face | 30–50 | 1–2 | 3–15 | effective rate ≧80% |
| trigeminal neuralgia | lesion | 30–50 | 1–2 | 3–15 | e.r. ≧85% |
| sciatica | lesion | 30–50 | 1–2 | 3–15 | e.r. ≧85% |
| epilepsy | head, brain, feet, cervical vertebrae | 30–50 | 1–2 | 3–30 | e.r. ≧90% |
| sequelae of brain damage | lesion | 30–50 | 1–2 | 3–30 | e.r. ≧80% |
| psychosis and hysteria | head, whole body | 30–50 | 1–2 | 30 | e.r. ≧70% |
| neurosis | head, vertebra, abdomen, feet | 30–50 | 1–2 | 3–30 | e.r. ≧70% |
| neurasthenia | head, vertebra, abdomen, feet | 30–50 | 1–2 | 3–30 | e.r. ≧70% |
| hysteria | head, vertebra, abdomen, feet | 30–50 | 1–2 | 3–30 | e.r. ≧70% |
| schizophrenia | head, vertebra, abdomen, feet | 30–50 | 1–2 | 3–30 | e.r. ≧70% |
| senile dementia | brain, whole body | 20–40 | 1–2 | 30 | remission |
| herpes simplex | lesion | 20–40 | 1–3 | 5–10 | effective rate ≧95% |
| herpes zoster | lesion | 20–40 | 1–3 | 5–10 | e.r. ≧95% |
| pustule | lesion | 20–40 | 1–3 | 5–10 | e r. ≧95% |
| folliculitis | lesion | 20–40 | 1–3 | 5–10 | e.r. ≧95% |
| syphilis | lesion | 30–60 | 1–2 | 30 | remission |
| tinea | lesion | 30–60 | 1–2 | 10–30 | effective rate ≧85% |
| coccidiomycosis | lesion | 30–60 | 1–2 | 10–30 | e.r. ≧85% |
| aspergillosis | lesion | 30–60 | 1–2 | 10–30 | e.r. ≧90% |
| scabies | lesion | 30–60 | 1–2 | 10–30 | e.r. ≧90% |
| allergic dermatitis, eczema | lesion | 30–60 | 1–2 | 10–30 | e.r. ≧90% |
| pruritus | lesion | 30–60 | 1–2 | 10–30 | e.r. ≧90% |
| softening of corn | lesion | 30–60 | 1–2 | 10–30 | e.r. ≧90% |
| actinic dermatitis | lesion | 30–60 | 1–2 | 10–30 | e.r. ≧80% |
| frostbite | lesion | 30–60 | 1–2 | 2–7 | e.r. ≧98% |
| cold injury | lesion | 30–60 | 1–2 | 2–7 | e.r. ≧90% |
| psoriasis | lesion | 30–60 | 1–2 | 10–30 | e.r. ≧80% |
| pityriasis rosea | lesion | 30–60 | 1–2 | 10–30 | e.r. ≧70% |
| erythema multiforme | lesion | 30–60 | 1–2 | 10–30 | e.r. ≧90% |
| allergic nocular vasculitis of skin | lesion | 30–60 | 1–2 | 10–30 | e.r. ≧70% |
| Behcet's disease | lesion | 30–60 | 1–2 | 30 | e.r. ≧70% |
| lupus erythematosus | lesion | 30–60 | 1–2 | 30 | remission |
| scleroderma | lesion | 30–60 | 1–2 | 30 | remission |
| vitiligo | lesion | 30–60 | 1–2 | 30 | remission |
| chloasma | lesion | 30–60 | 1–2 | 30 | effective rate ≧70% |
| acne | lesion | 30–60 | 1–2 | 30 | e.r. ≧70% |
| dermatitis | lesion | 20–50 | 1–2 | 30 | e.r. ≧80% |

TABLE B-continued

Functions and Therapeutic Effects of the Apparatus of the Present Invention

| Diseases | sites of treatment | Min./ time | times/ day | days/ course | therapeutic effects |
|---|---|---|---|---|---|
| seborrhaeica alopecia | lesion, accompanied with medication | 20–50 | 1–2 | 30 | e.r. ≧85% |
| osmidrosis | axilla, whole body | 20–50 | 1–2 | 30 | remission |
| anhidrosis | axilla, undersides of feet, whole body | 20–50 | 1–2 | 30 | remission |
| keloid | lesion | 20–40 | 1–3 | 30 | remission |
| acute hemorrhagic conjunctivitis | both eyes | 20–40 | 1–3 | 1–7 | effective rate ≧80% |
| ciliary blepharitis | lesion | 20–40 | 1–3 | 5–30 | e.r. ≧90% |
| conjunctivitis | lesion | 20–40 | 1–3 | 3–15 | e.r. ≧90% |
| scleritis | lesion | 20–40 | 1–2 | 5–20 | e.r. ≧60% |
| glaucoma | lesion | 20–40 | 1–2 | 30 | remission |
| juvenile myopia | lesion | 20–40 | 1–2 | 30 | effective rate ≧90% |
| presbyopia | lesion | 20–40 | 1–2 | 30 | remission |
| rhinitis | lesion | 20–40 | 1–2 | 30 | effective rate ≧80% |
| atrophic and allergic sinusitis | lesion | 20–40 | 1–2 | 30 | e.r. ≧80% |
| pharyngitis and laryngitis | lesion | 20–40 | 1–2 | 30 | e.r. ≧80% |
| tonsillitis | lesion | 20–40 | 1–2 | 30 | e.r. ≧80% |
| otitis media- | lesion | 20–40 | 1–2 | 5–30 | e.r. ≧85% |
| inflammation or furuncle of external auditory canal | lesion | 20–40 | 1–2 | 3–10 | e.r. ≧85% |
| toothache, hemorrhage | lesion | 20–40 | 1–2 | 3–20 | e.r. ≧70% |
| pulpitis | lesion | 20–40 | 1–2 | 30 | e.r. ≧60% |
| AIDS | whole body, chest, liver, abdomen, spleen, lymph, feet, head | 30–60 | 1–3 | 30 | e.r. ≧80% |
| tumors | lesions, whole body | 30–60 | 1–3 | 30 | remission |
| protection of radiation | whole body | 20–60 | 1–3 | 1–30 | effective rate ≧75% |
| delay of senility | whole body | 20–45– | 1–2 | 30 | e.r. ≧70% |
| human health care | whole body | 20–60 | 1–3 | 30 | e.r. ≧95% |
| elimination of fatigue, restoration of physical ability | kidney region, feet, abdomen, head | 20–50 | 1–2 | 5–20 | e.r. ≧90% |
| thyroidism | thyroid region, abdomen, stomach, feet, liver, whole body | 20–50 | 1–2 | 30 | e.r. ≧70% |

We claim:

1. An apparatus for regulating and improving status of growth and survival of a living organism comprising:

energy generating means;

means for receiving energy generated by said energy generating means and for generating at least one of thermal and magnetic energy; and a volume of a transducing material for generating a first electromagnetic radiation and a second electromagnetic radiation when excited by said at least one of thermal and magnetic energy produced by said means for receiving energy, the first radiation having a wavelength in range from about 0.2 $\mu$m to about 20 $\mu$m, and the second radiation having a wavelength in range from about 75,000 $\mu$m to about 100,000 $\mu$m, and wherein the means for generating the first electromagnetic radiation and the second electromagnetic radiation generates substantially no electromagnetic radiation having a wavelength in a range from about 20 $\mu$m to about 75,000 $\mu$m, said transducing material being substantially composed of:

one or a plurality of materials and compounds thereof selected from a group consisting of:

Co, Cu, Mo, Li, Be, BeO, Be$_2$C, Be$_3$N$_2$, B, B$_2$O$_3$, B$_4$C, BN, Mg, MgO, MgF$_2$, Al, Al$_2$O$_3$, Si, SiO$_2$, NbC, NbN, K, KO, Ca, CaO, Ti, TiO$_2$, TiC, TiN, TiB$_2$, V, V$_2$O$_5$, VC, VN, VB$_2$, Cr, Cr$_3$C$_2$, CrN, CrB, Cr$_3$B$_4$, Mn, MnO$_2$, MnF$_2$, Fe, Fe$_2$O$_3$, Ni, NiO, Zn, ZnO, ZnF$_2$, Ge, GeO, Sr, SrO, Zr, ZrO$_2$, ZrC, ZrN, ZrB$_2$, Nb, NbC, NbN, NbB$_2$, Ta, TaC, TaN, TaB$_2$, Hf, HfO$_2$, HfC, HfN, HfB, Se, Tn, TnO$_2$, TnC, TnN, TnB$_4$, TnB$_6$, W, WcW$_2$C, WB, Ce, CeO$_2$, Au, Y, and Y$_2$O$_3$, including a main constituent selected from the group consisting of chromium, magnesium, selenium, germanium, zinc, copper, manganese, aluminum, strontium, cerium, yttrium, calcium, titanium, cobalt, vanadium, molybdenum, silicon, iron, and compounds thereof, said main constituent constituting at least 50% of the content of said transducing material of said volume of transducing material.

* * * * *

UNITED STATES PATENT AND TRADEMARK OFFICE
CERTIFICATE OF CORRECTION

PATENT NO. : 5,814,078
DATED : Sep. 29, 1998
INVENTOR(S) : Lin Zhou; Xue-shan Zhang It is certified that error appears in the above-identified patent and that said Letters Patent is hereby corrected as shown below:

Cover Page, U.S. Patent Documents, line 11, change "Salia-Manoz" to --Salia-Munoz--

Cover Page, U.S. Patent Documents, line 13, change "4,588,700" to --4,558,700--

Cover Page, Other Publications, line 1, after "p. 467, 128,395, Federal Register --

Cover Page, Other Publications, lines 4 and 5, after "China" change "Certificate of the clinical application and basic scientific research" to --Certificate of the Clinical Application and Basic Scientific Research--

Col. 2, line 45, after "may" delete the second occurance of --also be--

Col. 8, line 2, after "(0.45--$10^5$ μm)" insert a period

Col. 9, line 4, before "be replaced" change "an" to --can--

Col. 9, line 49, after "as" change "show" to --shown--

Col. 13, lines 1-10, please replace lines 1-10 with the following:

| | |
|---|---|
| chromium oxide 95% | ferric oxide > 0.5% |
| chromium ≥ 0.8% | zinc oxide ≥ 0.4% |
| copper oxide ≥ 0.1% | cobalt oxide ≥ 0.1% |
| manganese oxide ≥ 0.1% | molybdenum oxide > 0.1% |
| selenium oxide ≥ 0.7% | strontium oxide ≥ 0.1% |

UNITED STATES PATENT AND TRADEMARK OFFICE
CERTIFICATE OF CORRECTION

PATENT NO. : 5,814,078
DATED : Sep. 29, 1998
INVENTOR(S) : Lin Zhou; Xue-shan Zhang It is certified that error appears in the above-identified patent and that said Letters Patent is hereby corrected as shown below:

vanadium oxide ≥ 0.1%        aluminum oxide ≥ 0.1%
magnesium oxide ≥ 0.1%       silicon oxide ≥ 0.1%
germanium oxide ≥ 0.6%       lanthanium ≥ 0.1%
boric oxide ≥ 0.1%           magnesium fluoride ≥ 0.1%

Col. 14, lines 4-13, please replace lines 4-13 with the following:

chromium oxide 93%           ferric oxide ≥ 0.5%
chromium > 0.8%              zinc oxide ≥ 0.5%
copper oxide ≥ 0.1%          cobalt oxide > 0.1%
manganese oxide ≥ 0.1%       molybdenum oxide > 0.1%
selenium oxide ≥ 1%          strontium oxide ≥ 0.1%
vanadium oxide > 0.1%        aluminum oxide ≥ 0.1%
magnesium oxide > 0.1%       silicon oxide ≥ 0.1%
germanium oxide ≥ 0.1%       lanthanium > 0.1%
magnesium fluoride ≥ 0.1%

Col. 14, lines 53-60, please replace lines 53-60 with the following:

chromium oxide 94%           ferric oxide ≥ 0.5%
chromium ≥ 0.8%              zinc oxide ≥ 0.7%
copper oxide ≥ 0.2%          cobalt oxide ≥ 0.2%
manganese oxide > 0.3%       molybdenum oxide ≥ 0.1%
selenium oxide ≥ 0.9%        strontium oxide ≥ 0.1%
vanadium oxide > 0.1%        aluminum oxide ≥ 0.1%
magnesium oxide ≥ 0.1%       silicon oxide ≥ 0.1%
germanium oxide ≥ 0.1%       lanthanium ≥ 0.1%
$CaCO^3$ > 0.1%

UNITED STATES PATENT AND TRADEMARK OFFICE
CERTIFICATE OF CORRECTION

PATENT NO. : 5,814,078
DATED : Sep. 29, 1998
INVENTOR(S) : Lin Zhou; Xue-shan Zhang It is certified that error appears in the above-identified patent and that said Letters Patent is hereby corrected as shown below:

Col. 15, lines 54-62, please replace lines 54-62 with the following:

chromium oxide 94%     ferric oxide > 0.5%
chromium ≥ 0.8%        zinc oxide > 0.8%
copper oxide ≥ 0.2%    cobalt oxide > 0.2%
manganese oxide ≥ 0.3% molybdenum oxide ≥ 0.1%
selenium oxide ≥ 0.9%  strontium oxide > 0.1%
vanadium oxide ≥ 0.1%  aluminum oxide > 0.1%
magnesium oxide > 0.1% silicon oxide > 0.1%
germanium oxide ≥ 0.8% lanthanium ≥ 0.1%
KI > 0.1%              $BO^2$ ≥ 0.1%
$CaCO^2$ ≥ 0.1%        $MgF^2$ ≥ 0.1%

Col. 22, line 23, after "The" change "function" to --functions--

Col. 25, line 36, after "example," change "the" to --they--

Col. 26, line 36, before "least" change "a" to --at--

Col. 27, line 1, after "by -amylase" delete --and -amylase--

Col. 27, line 22, before "the seeds" change "form" to --from--

Col. 40, line 55, after "Nb," delete --NbC, NbN--

UNITED STATES PATENT AND TRADEMARK OFFICE
CERTIFICATE OF CORRECTION

PATENT NO. : 5,814,078

DATED : Sep. 29, 1998

INVENTOR(S) : Lin Zhou; Xue-shan Zhang

It is certified that error appears in the above-identified patent and that said Letters Patent is hereby corrected as shown below:

Col. 27, line 22, before "the seeds" change "form" to --from--

Col. 40, line 55, after "Nb," delete --NbC, NbN--

Signed and Sealed this

Seventh Day of March, 2000

Q. TODD DICKINSON

Attest:

Attesting Officer

Commissioner of Patents and Trademarks